US012603171B2

(12) United States Patent
Roth

(10) Patent No.: US 12,603,171 B2
(45) Date of Patent: Apr. 14, 2026

(54) FACILITATING REMOTE CONFIGURATION

(71) Applicant: Roche Diagnostics Operations, Inc.,
Indianapolis, IN (US)

(72) Inventor: Andre Roth, Lucerne (CH)

(73) Assignee: Roche Diagnostics Operations, Inc.,
Indianapolis, IN (US)

( * ) Notice: Subject to any disclaimer, the term of this
patent is extended or adjusted under 35
U.S.C. 154(b) by 304 days.

(21) Appl. No.: 18/596,708

(22) Filed: Mar. 6, 2024

(65) Prior Publication Data

US 2024/0304318 A1 Sep. 12, 2024

(30) Foreign Application Priority Data

Mar. 10, 2023 (EP) ..................................... 23161335

(51) Int. Cl.
_G16H 40/40_ (2018.01)
(52) U.S. Cl.
CPC .................................. _G16H 40/40_ (2018.01)
(58) Field of Classification Search
None
See application file for complete search history.

(56) References Cited

U.S. PATENT DOCUMENTS 8,914,794 B2 * 12/2014 Bliss .......................... G06F 8/63
717/121
11,695,585 B2 * 7/2023 Ansari ................ H04L 12/2812
709/225

11,829,744 B2 * 11/2023 Hansen ...................... G06F 8/54
2008/0140723 A1 * 6/2008 Hernandez ............. G16H 30/20
2008/0208375 A1 * 8/2008 Grgic ................... G05B 19/042
700/86
2009/0228512 A1 * 9/2009 Chopra ..................... G06F 8/71
707/999.102
2022/0197632 A1 * 6/2022 Cg ............................. G06F 8/71
2024/0045667 A1 * 2/2024 Hansen ...................... G06F 8/65
(Continued)

FOREIGN PATENT DOCUMENTS

EP 2541396 A2 1/2013
WO WO-2008025496 A1 * 3/2008 ............... G06F 8/71
WO WO-2013020045 A2 * 2/2013 ............... H04W 4/70

OTHER PUBLICATIONS

Sun, "Software as a Service: Configuration and Customization
Perspectives", 2008, IEEE (Year: 2008).*
(Continued)

*Primary Examiner* — Hossain M Morshed
(74) *Attorney, Agent, or Firm* — Lee & Hayes, P.C.

(57) ABSTRACT

A computer implemented method of a design enterprise
network for facilitating remote configuration of a software
instance comprised in a laboratory enterprise network,
wherein the laboratory enterprise network is communicably
coupled to an in vitro diagnostics (IVD) network, wherein
the IVD network comprises at least one IVD instrument, and
wherein the computer implemented method comprises
obtaining by a generator computing instance comprised in a
design enterprise network, a configuration definition input
for configuring the software instance and generating, by the
generator computing instance comprised in the design enter-
prise network, a configuration object based on the configu-
ration definition input.

14 Claims, 12 Drawing Sheets

(56)             References Cited

U.S. PATENT DOCUMENTS

2024/0304318 A1 *   9/2024   Roth ......................... G06F 8/60

OTHER PUBLICATIONS

Paul, "Service-Oriented Architecture for Command and Control Systems with Dynamic Reconfiguration", 2004, Arizona State University (Year: 2004).*
European Search Report issued Aug. 4, 2023, in Application No. 23161335.7, 2 pp.

* cited by examiner

1

2

20ana

20ana

20ana

20ana

20ana

20ana

20post

20trans

20pre

20pre

6

4

3

5

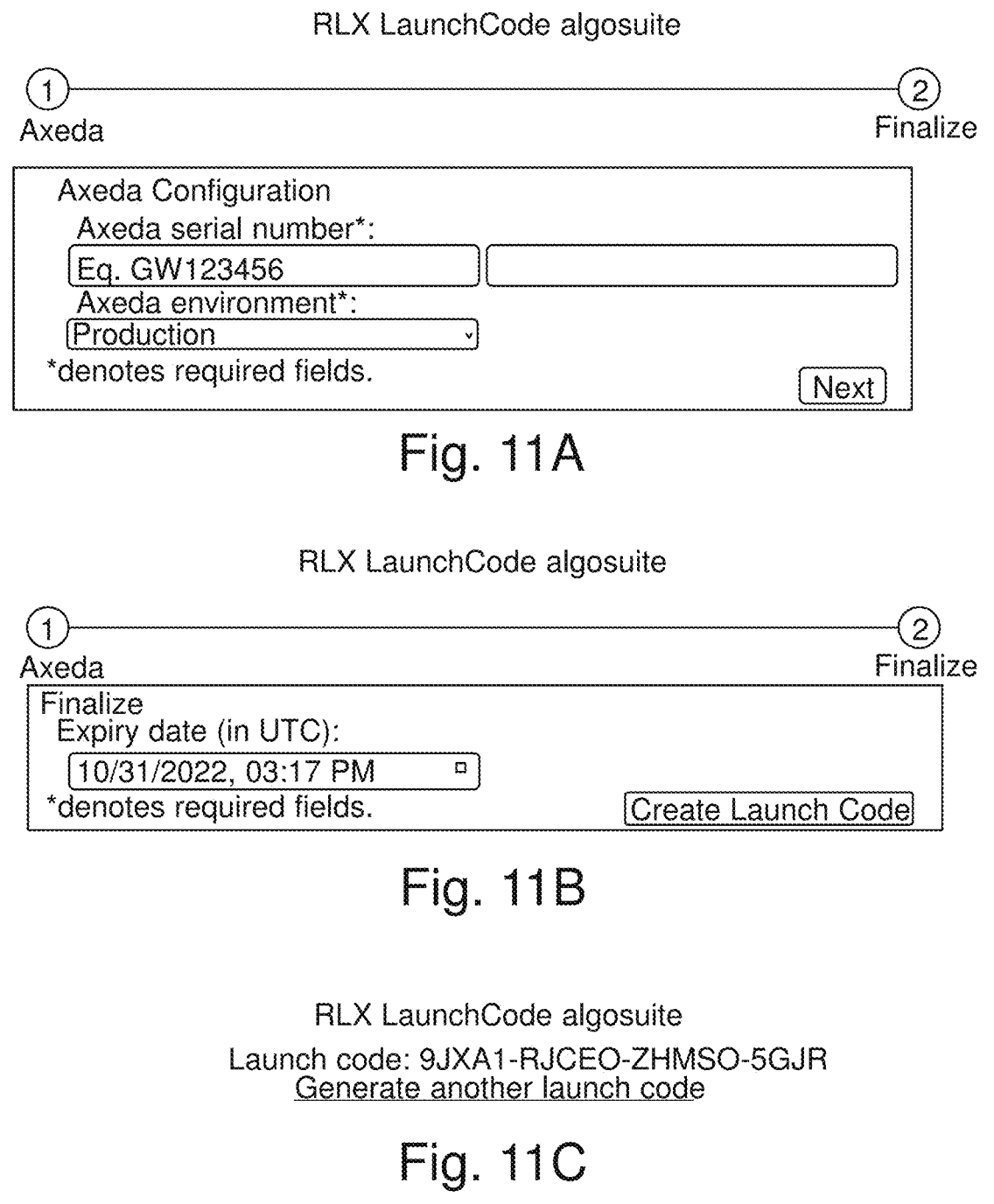

RLX LaunchCode algosuite

① ————————————————————————————————— ②
Axeda                                                          Finalize Axeda Configuration
    Axeda serial number*:
    [ Eg. GW123456 ]                    [                    ]
    Axeda environment*:
    [ Production                    ˅ ]
*denotes required fields.
                                                [ Next ]

Fig. 11A

RLX LaunchCode algosuite

① ————————————————————————————————— ②
Axeda                                                          Finalize Finalize
    Expiry date (in UTC):
    [ 10/31/2022, 03:17 PM        ▫ ]
*denotes required fields.            [ Create Launch Code ]

Fig. 11B

RLX LaunchCode algosuite
Launch code: 9JXA1-RJCEO-ZHMSO-5GJR
Generate another launch code

Fig. 11C

FACILITATING REMOTE CONFIGURATION

CROSS-REFERENCE TO RELATED APPLICATIONS

This application claims priority to European Application No. 23161335.7, filed Mar. 10, 2023, the disclosure of which is hereby incorporated by reference in its entirety.

TECHNICAL FIELD

This disclosure relates to a computer implemented method of a design enterprise network for facilitating remote configuration of a software instance comprised in a laboratory enterprise network, a computer implemented method for facilitating remote configuration of a software instance in a laboratory enterprise network, and an associated system, apparatuses, computer readable media, and computer program elements.

BACKGROUND

An in vitro diagnostic (IVD) analysis laboratory is capable of analysing a large number of patient samples. A sample can potentially comprise at least one analyte of interest, for example, molecules, ions, proteins, metabolites, pathogens, and the like. It is typically one of the tasks of IVD testing to detect the presence, absence and/or a concentration of one or more analytes in a sample. More generically, IVD testing can refer to determining a biological property of a sample. IVD testing can comprise performing at least one analytical test on a sample, wherein the analytical test can allow conclusions about the biological properties of the sample to be drawn. The analytical test can, for example, comprise adding a reagent to the sample, a possible detectable reaction of the sample with the reagent, and/or a detecting or non-detection of this reaction. Detecting of a reaction can, for example, comprise measuring a physical value of the sample (resp. a composite obtained by using the sample such as a sample-reagent mixture), such as a spectrum and/or an intensity of a radiation reflected by and/or transmitted through the sample (resp. the composite obtained by using the sample). Point-of-care (POC) devices capable of performing similar tests on samples, but have a lower throughput.

IVD laboratories are complex and custom-designed based on requirements of each laboratory The installation of equipment in an IVD laboratory and its initial configuration and testing involves the tuning of hundreds or thousands of software parameters based in the firmware of individual analyser machines, middleware instances configured to control the analyser machines, or laboratory information management system (LIMS) configured to control the overall laboratory through the middleware instances and to deliver sample analysis results.

Therefore, the configuration and testing of an IVD laboratory can last several months, requiring staff from the manufacturer of the IVD laboratory equipment to be permanently present to make relatively minor occasional changes to the configuration of software or firmware, for example. Networks of point-of-care devices can present a configuration challenge because typically large number of POC devices, distributed throughout the hospital, may require a simultaneous software upgrade. In practice, the update of a large number of POC devices may require a site visit from a service engineer. Accordingly, configuration, testing, and maintenance approaches to IVD laboratory equipment and/or POC devices can be improved.

SUMMARY

In some embodiments, there is provided a computer implemented method of a design enterprise network for facilitating remote configuration of a software instance comprised in a laboratory enterprise network. The laboratory enterprise network is communicably coupled to an in vitro diagnostics, IVD, network. The IVD network comprises at least one IVD instrument. The computer implemented method includes:

obtaining, by a generator computing instance comprised in a design enterprise network, a configuration definition input for configuring the software instance;

generating, by the generator computing instance comprised in the design enterprise network, a configuration object based on the configuration definition input, wherein the configuration object comprises computer readable data which is interpretable by the software instance of the laboratory enterprise network to define a configuration of the software instance;

generating, by the generator computing instance comprised in the design enterprise network, a configuration identifier, wherein the configuration identifier is logically linked to the configuration object; and storing the configuration object in a host, wherein the host is communicably coupled to the design enterprise network and the laboratory enterprise network.

An example of an IVD instrument is an IVD analytical instrument.

In some embodiments, there is provided computer implemented method for facilitating remote configuration of a software instance in a laboratory enterprise network. The laboratory enterprise network is communicably coupled to an in vitro diagnostics, IVD, network. The IVD network comprises at least one in vitro diagnostic, IVD, instrument. The method comprises:

obtaining, by the software instance comprised in the laboratory enterprise network, a configuration identifier generated by a generator computing instance of a design enterprise network;

transmitting the configuration identifier, by the software instance of the laboratory enterprise network, to a host that is communicably coupled to the design enterprise network and the laboratory enterprise network;

receiving, from the host, a configuration object that is logically linked to the configuration identifier, wherein the configuration object comprises computer readable data which is interpretable by the software instance of the laboratory enterprise network that defines a configuration of the software instance of the laboratory enterprise network, and wherein the configuration object has been generated by the generator computing instance of the design enterprise network according to a configuration definition input defining configuration data for facilitating the configuration of the software instance of the laboratory enterprise network;

configuring the software instance of the laboratory enterprise network according to the computer readable data of the configuration object; and operating the software instance.

In some embodiments, there is provided a generator computing device comprising a communications interface, a memory, and a processor. The processor is configured to perform the computer implemented method according to the first aspect, or its embodiments.

In some embodiments, there is provided a computing device comprising a communications interface, a memory, and a processor. The processor is configured to perform the computer implemented method according to the second aspect, or its embodiments.

In some embodiments, there is provided a system. The system comprises:

a design enterprise network, wherein the design enterprise network comprises a gateway, and a generator computing instance communicably coupled to the gateway. The generator computing instance is configured to perform the computer-implemented method the first aspect, or its embodiments.

The system further comprises a laboratory enterprise network. The laboratory enterprise network comprises a gateway, and a computing device communicably coupled to the gateway. The computing device is configured to host a software instance communicably coupled to the gateway of the laboratory enterprise network. The software instance is configured to perform the computer-implemented method according to the second instance, or its embodiments.

The system further comprises an IVD network. The IVD network comprises an IVD instrument, for example, an IVD laboratory instrument or an POC device, and an IVD network gateway. In some cases, the IVD network gateway may be part of the IVD instrument. The IVD network is communicably coupled to the laboratory enterprise network.

The system further comprises a host. The host comprises a host gateway, and a data store communicably coupled to the host gateway via a host network.

The system further comprises a communication network configured to communicably couple the design enterprise network, the laboratory enterprise network, the host, and the IVD network comprising the IVD instrument.

In some embodiments, there is provided a method of operating a system according to the fifth aspect comprising the computer implemented methods of the first aspect, and the second aspect.

In some embodiments, there is provided a computer program element comprising computer-readable instructions which, when being executed by a computer, performs the computer implemented method according to one of the first or second aspects, or their embodiments.

In some embodiments, there is provided a computer readable medium comprising the computer program element of the seventh aspect.

Some embodiments are defined in the claims, to which the reader may now refer, and which are discussed further in this specification.

An effect of the approach of the foregoing aspects is that of improving security, because final configuration of an IVD network may be performed by a remote team of IT professionals over a secure link. A reduction in the complexity of configuring software on the laboratory enterprise network is also possible, because the standard install media can be used by IT professionals at the customer, rather than requiring field service software professionals of the manufacturer to be physically located at the customer site. Transferring customised installation software from the design enterprise network to the laboratory enterprise network could involve putting security credentials, and IVD analyser software or firmware configurations into an uncontrolled domain (for example, if the customised install media containing such customised installers are lost or mislaid).

According to the present disclosure, the initial installation of operating software on at least one software instance hosted in the laboratory enterprise network (for example, a network that is communicably coupled to an IVD network comprising a plurality of IVD analysers, for example, IVD laboratory analysers and/or POC analysers) involves defining how a typical standardised software instance to be located at a laboratory enterprise network to can defined in configuration data. As an example, the design of the laboratory enterprise network may involve a software instance configured to host a remote access program. The remote access program allows a remote network to connect to the IVD network via the laboratory enterprise network, so that users of the remote network can perform further configuration of the IVD network, or maintenance or security sweeps of the IVD network. In this case, the configuration data may comprise login details and network details that the standard version of the remote access program should be programmed with at the software instance of the laboratory enterprise network, to enable remote access.

Standard software installation is, therefore, performed by IT professionals of the customer on a software instance of the laboratory enterprise network. Thus, specially customised software does not, initially, need to be provided for installation on a software instance of the laboratory enterprise network. Specially customised install files, such as .iso's or virtual machines, do not need to be produced for each customer installation. Initially, the standard installation of a software package can be followed, rather than requiring special customisation to the particular IVD network design.

Following successful installation of the standardised software on at least one software environment of the laboratory enterprise network, the laboratory enterprise network therefore prompts the design enterprise network or a related network to make available data that can be used to configure the at least one software instance in the laboratory enterprise network. In practice, the design enterprise network can store this configuration data on a host (such as a cloud computing service).

The configuration data can be requested in the laboratory enterprise network using a configuration identifier generated in the design enterprise network at the time the customer IVD network design is performed. The configuration identifier is logically associated with, or references, the configuration data during design of a relevant IVD system to be connected to the laboratory enterprise network.

The configuration identifier is provided to the laboratory IT engineers, for example, when the standardised installation software for the IVD network is transferred. The configuration identifier can be an alphanumeric code provided on a slip of paper, for example. Following installation of the standard software, the laboratory IT engineers are prompted to, and enter, the configuration identifier into a prompt (provided, for example, in an installation website accessed from within the second network). The configuration data is automatically downloaded to the at least one software instance of the laboratory enterprise network from the host. The configuration data is, for example, used to configure software and/or firmware modules of at least one software or hardware instance hosted by the laboratory enterprise network. Following the automatic configuration of such a remote access application, IT engineers situated at the manufacturer can then remotely configure an apparatus and the second network without requiring intervention from the laboratory IT engineer.

The laboratory enterprise network is communicably coupled to an in vitro diagnostics, IVD, network. The IVD network comprises at least one in vitro diagnostic, IVD, instrument. Accordingly, operation of the software or hardware instance of the laboratory enterprise network following configuration of the software instance using the configuration data enables the software or hardware instance of the laboratory enterprise network to be operated to perform actions in the IVD network. For example, the software or hardware instance of the laboratory enterprise network is configured, by the configuration data, to enable remote access of a secure remote computer into the IVD network via the laboratory enterprise network. The software or hardware instance may enable a secure remote computer to connect to one or more IVD instruments of the IVD network. Following connection of the secure remote computer to one or more IVD instruments of the IVD network, the secure remote computer may be used to configure network setting of the IVD network, to download or to upload data to at least one IVD instrument of the IVD network, or to extract log files or usage data of individual IVD instruments. The software or hardware instance may enable a secure remote computer to monitor physical parameters of the at least one IVD instrument of the IVD network. For example, the monitored physical parameters may comprise one, or more, of a temperature measurement, vibration measurement, noise measurement, image or video of a part of the IVD instrument, an audio recording obtained in the vicinity of the IVD instrument, quality of service metrics obtained from robotic equipment or from a laser measuring device, and the like.

In examples, different configuration identifiers may be provided in respect of different apparatus types in the IVD network. A master configuration identifier may be provided enabling access to all apparatus types in the IVD network, as well as networking equipment, servers, computers, and gateways necessary for controlling the IVD network from the software instance of the laboratory enterprise network. In some examples, the configuration identifier is valid only once. In other words, when the laboratory IT engineer enters the configuration identifier into the prompt, the host delivers the configuration information to the laboratory enterprise network. The host simultaneously deletes the configuration information from its own data store. Alternatively, a flag may be set in the host blocking further download of the configuration information from the host. This enhances security because proliferation of the specific configuration of the laboratory enterprise network and the IVD network is prevented. Alternatively, the configuration identifier can be time limited by the design enterprise network during IVD network design, so that attempting to use the configuration identifier to download configuration information from the host after a predetermined deadline is unsuccessful.

Certain terms will be used in this patent application, the formulation of which should not be interpreted to be limited by the specific term chosen, but as to relate to the general concept behind the specific term.

As used herein, the terms "comprises", "comprising", "includes", "including", "has", "having", or any other variation thereof, are intended to cover a non-exclusive inclusion.

An "in vitro diagnostic" (IVD) instrument, can comprise one or more analytical modules designed to execute respective workflows that are optimized for certain types of analysis.

The IVD instrument can include analytical apparatuses for one or more of clinical chemistry, immunochemistry, coagulation, haematology, etc. An IVD instrument can for example be an IVD laboratory instrument or a POC device.

Thus, the IVD instrument may comprise one analytical module or a combination of any of such modules with respective workflows, where pre-analytical and/or post analytical modules may be coupled to individual analytical modules or be shared by a plurality of analytical modules. Alternatively, pre-analytical and/or post-analytical functions may be performed by units integrated in an IVD analytic apparatus. The IVD instrument can comprise functional units such as liquid handling units for pipetting and/or pumping and/or mixing of samples and/or reagents and/or system fluids, and also functional units for sorting, storing, transporting, identifying, separating, and detecting.

The term "sample" refers to a biological material suspected of containing one or more analytes of interest and whose detection, qualitative and/or quantitative, may be associated to a particular condition (for example, a clinical condition).

The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The sample can be pre-treated prior to use, such as preparing plasma from blood, diluting viscous fluids, lysis or the like; methods of treatment can involve filtration, centrifugation, distillation, concentration, inactivation of interfering components, and the addition of reagents. A sample may be used directly as obtained from the source in some cases or following a pre-treatment and/or sample preparation workflow to modify the character of the sample, for example, after adding an internal standard, after being diluted with another solution or after having being mixed with reagents for example, to enable carrying out one or more in vitro diagnostic tests, or for enriching (extracting/separating/concentrating) analytes of interest and/or for removing matrix components potentially interfering with the detection of the analyte(s) of interest.

The term "Point of Care" POC or "Point of Care environment" as used herein is defined to mean a location on or near a site of patient care where medical or medically related services such as medical testing and/or treatment are provided, including but not limited to hospitals, emergency departments, intensive care units, primary care setting, medical centres, patient homes, a physician's office, a pharmacy, or a site of an emergency.

Point of care testing encompasses analysis of one or more patient sample(s) in a point of care environment, which is typically accomplished through the use of POC devices/instruments, for example, transportable, portable, and handheld instruments, but small bench analysers or fixed equipment can also be used when a handheld device is not available—the goal being to collect the patient sample and obtain the analytical data in a (relatively) short period of time at or (relatively) near the location of the patient.

A "network" in the present disclosure refers to a plurality, for example, one or more, or two or more, connected devices with data communication capabilities. The connected devices in a network can be designated by being managed by a particular organization. In an example, the "network" can also be considered to be a domain, which is an administrative grouping of networks managed by one or more domain controllers. For instance, a network can be a hospital network, a laboratory enterprise network, a network of a manufacturer or a network of a remote support engineer. A laboratory enterprise network is communicably coupled to a network of IVD instruments, but the laboratory enterprise network itself comprises no specialised equipment such as hardware analysers. In some embodiments, the laboratory enterprise network comprises or hosts analysis software that uses results obtained from instruments of the network of IVD instruments. In some embodiments, the network can be constituted by a set of devices, such as IVD instruments, IVD laboratory middleware, or IVD analytical devices which form a logical group (for example, a network or domain of devices of a particular organization as defined above). In addition or alternatively, the devices in a network can be located in relatively close spatial relationship (for example, a campus, a laboratory or a hospital building). The devices of the network can be connected by a local area network. However, in other embodiments the devices of the network can be located at two or more remote locations (for example, two different sites of a hospital).

The term "install" (in the context of data packages) is not limited to any particular operation of modifying or updating a software of a computing device (for example, a PC; a server, an apparatus/device comprising a microcontroller and memory, for example, an IVD device such as an IVD laboratory instrument or a POC device), or cloud instance. Rather, the term "install" encompasses any operation in which data included in a data package is incorporated/deployed in one of those listed instances (directly or after processing steps such as unpacking or compilation). For example, a data package might include information that is in some way or form used in operating the instance. In this situation, installing the data package might mean storing the information at a respective location to make it available to the instance. Further embodiments of how data packages can be installed on instances will be discussed below.

The term "communication network" as used herein encompasses any type of wired or wireless network, including but not limited to a WIFI, GSM, UMTS or other wireless digital network or a wired network, such as Ethernet, the Internet, or the like. For example, the communication network may include a combination of wired and wireless networks. For example, the status data of an IVD analyser may be transmitted over the communication network.

The term "gateway" encompasses any hardware-, firmware- and/or software-based module operable to execute program logic to allow communication with an external entity over a communications network (such as a server or another interface). A gateway can comprise networking hardware and/or software to allow data flow from one network to another. A gateway may act as a proxy server and/or a firewall. A gateway may restrict the access and/or data transfer from one network to another. A gateway may separate a domain or control from another domain of control, for example, the internet from an enterprise network or a first enterprise network from a second enterprise network.

The term "server" or "cloud" encompasses any physical machine or virtual machine having a physical or virtual processor, capable of accepting requests from and giving responses accordingly. It shall be clear to a person of ordinary skill in the art of computer programming that the term machine may refer to a physical hardware itself, or to a virtual machine such as a JAVA Virtual Machine (JVM), or even to separate virtual machines running different Operating Systems on the same physical machine and sharing that machine's computing resources. Servers can run on any computer including dedicated computers, which individually are also often referred to as "the server" or shared resources such as virtual servers. In many cases, a computer can provide several services and have several servers running. Therefore the term server shall encompass any computerized device that shares a resource to one or more client processes. The server can receive, process, and transmit analytical device status data.

The term "user interface" encompasses any suitable piece of software and/or hardware for interactions between an operator and a machine, including but not limited to a graphical user interface for receiving as input a command from an operator and also to provide feedback and convey information thereto. Also, a system/device may expose several user interfaces to serve different kinds of users/operators. The user interface may display analytical device status data.

According to some embodiments, the laboratory enterprise network 140 is not communicably coupled to an in vitro diagnostics, IVD, network.

According to some embodiments, the design enterprise network is a first network. According to an embodiment, the laboratory enterprise network is a second network.

According to an embodiment, the IVD network comprises at least one IVD instrument including at least one IVD analytic instrument, for example, a IVD laboratory analytic instrument or a POC (point of care) device.

According to some embodiments, the IVD network comprises one or more IVD instruments and a computing instance comprising a gateway. According to an example, the gateway is, for example, comprised in one of the IVD instruments. For example, the IVD instrument is a POC device comprising connectivity features (for example, wherein the connectivity features comprise access restrictions).

According, the laboratory enterprise network is communicably coupled to an IVD network.

BRIEF DESCRIPTION OF THE FIGURES

FIG. 11A schematically illustrates a dialog box for entering a configuration definition input.

FIG. 11B schematically illustrates setting an expiry time of an identifier.

FIG. 11C schematically illustrates a configuration identifier.

The figures are not drawn to scale, are provided as illustration only and serve only for better understanding but not for defining the scope of the invention. No limitations of any features of the invention should be inferred from these figures

DETAILED DESCRIPTION

Figure 1:
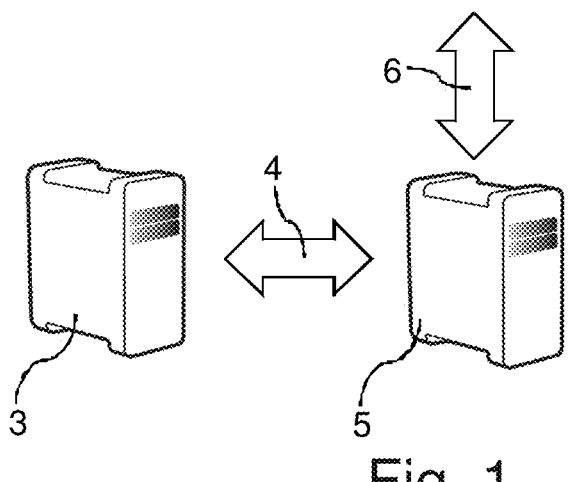
FIG. 1 schematically illustrates an exemplary plan view of an automated in vitro diagnostics (IVD) laboratory.

FIG. 1 schematically illustrates an exemplary plan view of an automated in vitro diagnostics (IVD) laboratory 1. The IVD laboratory 1 comprises a variety of IVD instruments 20*ana*, 20*post*, 20*trans*, 20*pre*. The IVD instruments 20*ana*, 20*post*, 20*trans*, 20*pre* are communicably coupled to form an IVD network 20 (shown in FIG. 2). A gateway 3 enables the IVD instruments 20*ana*, 20*post*, 20*trans*, 20*pre* to be communicably coupled, for example, to a laboratory enterprise network 140, to be described subsequently. In an embodiment, the laboratory enterprise network 140 and the IVD network 20 are comprised in a unified network domain 141, and/or are at the same geographical location. In other embodiments, the laboratory enterprise network 140 and the IVD network 20 are comprised in different network domains or are located at different geographical locations.

Processing a sample in an IVD laboratory 1 such as the one illustrated in FIG. 1 can, for example, comprise transporting the sample (typically in IVD containers such as IVD tubes; the IVD containers may be held in IVD container holders such as IVD tube racks), performing pre-analytical steps on the samples (for example, preparatory steps such as centrifuging), performing analytical steps on the samples (for example, adding a reagent to the sample and measuring the reaction of the sample with the reagent), and/or performing post-analytical steps on the samples (for example, storage of a sample in a refrigerator for later use).

The IVD laboratory instruments 20*ana*, 20*post*, 20*trans*, 20*pre* comprises one or more IVD laboratory instruments 20 designed for processing samples, for example, for performing one or more steps of an intended workflow on the sample. Processing a sample can comprise one or more physical processing steps (for example, moving, mixing, heating, etc.). The IVD laboratory instruments 20*ana*, 20*post*, 20*trans*, 20*pre* can comprise instrument hardware for processing samples (for example, gripper, reagent storage, pipetting apparatus, heating element, etc.) as well as instrument software designed for operating the instrument hardware. An IVD laboratory instrument 20*ana*, 20*post*, 20*trans*, 20*pre* can comprise a control unit designed for controlling, in particular steering, the operation of the instrument hardware, wherein the instrument software can be designed for being executed using the control unit.

IVD laboratory instruments 20*ana*, 20*post*, 20*trans*, 20*pre* are typically categorized according to the different type of sample processing steps they can perform. A transport IVD laboratory instrument 20*trans* is designed for transporting samples (resp. the IVD containers and/or respective holders), for example, from one IVD laboratory instrument to another. A pre-analytical IVD laboratory instruments 20*pre* is designed for performing pre-analytical steps on the samples. A analytical IVD laboratory instrument 20*ana* is designed for performing analytical steps (such as an analytical test) on the samples; an analytical IVD laboratory instrument 20*ana* can comprise a digital analytical IVD laboratory instrument designed for performing analytical computation steps (for example, a medical algorithm). A post-analytical IVD laboratory instrument 20*post* is designed for performing post-analytical steps on the samples. Some IVD laboratory instruments 20*ana*, 20*post*, 20*trans*, 20*pre* are capable of performing multiple type of sample processing steps, for example, pre-analytical and analytical steps.

In the example of FIG. 1, the IVD laboratory instrumentation 20*ana*, 20*post*, 20*trans*, 20*pre* comprises two pre-analytical IVD laboratory instruments 20*pre*, five analytical IVD laboratory instruments 20*ana*, one post-analytical IVD laboratory instruments 20*post*, and one transport IVD laboratory instruments 20*trans*, wherein the IVD laboratory instrumentation illustrated in FIG. 1 is designed such that the one transport IVD laboratory instruments 20*trans* connects all the other IVD laboratory instruments 20*ana*, 20*post*, 20*trans*, 20*pre*.

Figure 2:
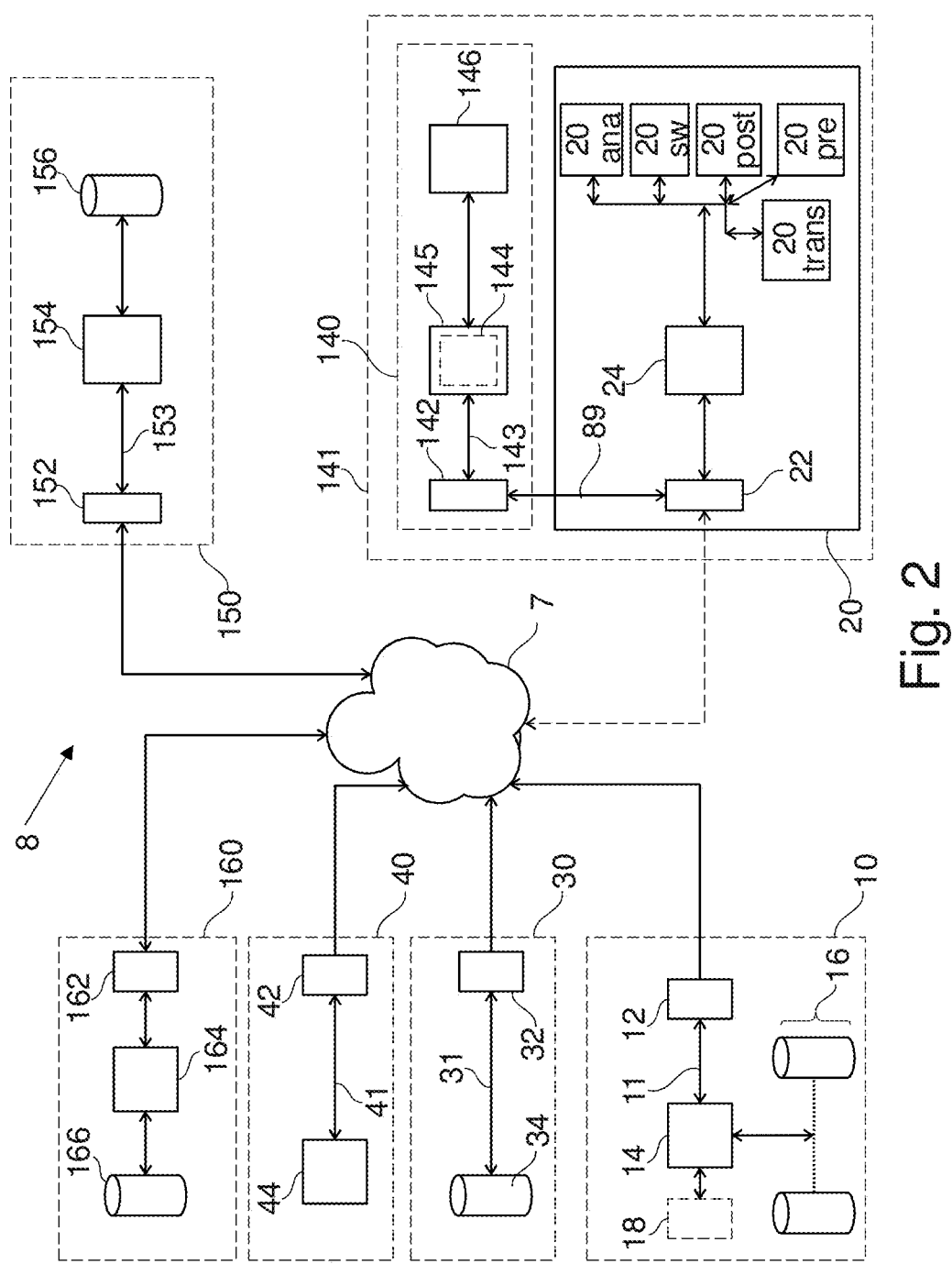
FIG. 2 schematically illustrates a system according to the fifth aspect.

A digital analytical IVD laboratory instrument 20*ana* can be provided by a computer, or a virtualised instance hosted by a hypervisor running on a computer or a bare metal server (20*sw* in FIG. 2). In other words, the analytical IVD laboratory instrument 20*ana* does not need to comprise mechanical parts or sensors. In some embodiments, digital analytical IVD laboratory instrument 20*ana* is configured to receive the results of analyses performed on other instruments of the IVD laboratory via internal IVD laboratory communications network 6.

In this example, the analytical IVD laboratory 1 may further comprise a middleware host 5 that is communicably coupled to laboratory information system (LIS) by a further communications network 4. The LIS 3, for example, interfaces with the middleware host 5 of the IVD laboratory 1 configured to operate the equipment of the IVD laboratory 1 based on service requests or workflows generated by the LIS 3. The LIS 3 may collect and store, or forward sample analysis results from digital analytical IVD laboratory instrument 20*ana* as they are generated. The LIS 3 may monitor reagent or consumable usage, and generate requests for new orders of reagents or consumables when current stocks of reagents or consumables are falling low. The LIS 3 may collect information concerning maintenance needs or analyser non-compliances and generate requests for engineering checks. Furthermore, the LIS 3 may gather information and generate statistics defining the performance of the overall IVD laboratory 1. The LIS 3 may host an information source, such as an embedded website, enabling laboratory staff and engineering staff to assess the performance of the IVD laboratory 3, or any apparatus within it.

The LIS 3 may comprise a gateway enabling communication, via a LAN or a WAN, with a further network or device, such as a laboratory enterprise network 140. For example, the gateway enables an external network to order tests from the IVD laboratory 1, or to request results of previously ordered tests from the IVD laboratory.

FIG. 2 schematically illustrates a system according to the fifth aspect.

The system 8 comprises a design enterprise network 10 controlled by a manufacturer or service provider. For example, the manufacturer may produce IVD laboratory instruments and/or point of care, POC, devices, and also further produce/configure software instances for laboratory enterprise networks. The laboratory enterprise networks may be controlled by the manufacturer's customer, for example, a laboratory enterprise or a hospital enterprise.

The software instances configured by the manufacturer in the design enterprise network 10 may be designed to—after having been deployed at the laboratory enterprise network—access and/or exchange data with the IVD instruments. The design and configuration of such software instances is, for example, at least partially performed by computing devices comprised within the design enterprise network 10. Often, the configuration takes the form of defining how a standard item of software, such as a remote access client, can be configured to work in a specific client network context. For example, a standard remote access server is not pre-populated with the remote network attributes that would enable a remote user to connect to the remote access server.

In an example, the design enterprise network 10 comprises a user interface 18 capable of receiving, in the design phase, a configuration definition input 62 for the software instance, for example, desired remote access attributes, such as login and/or network address attributes of one to IVD instruments in the IVD network (for example, an IVD laboratory network and/or a network of POC analysers). For example, a software architect may provide the configuration definition input 62 based on a system architecture of the IVD laboratory. A generator computing instance 14 of the design enterprise network 10 is capable of generating a configuration object 63 from the configuration definition input 62, as will be discussed in more detail subsequently.

The generator computing instance 14 of the design enterprise network 10 is also configured to generate a configuration identifier 68 that is linked to the configuration object 63. The design enterprise network 10 may comprise one or more data stores 16 with standard installation software intended for installation on a computing device 145, for example, of a laboratory enterprise network 140. The one or more datastores 16 may also comprise configuration templates of the standard installation software that can be customised according to the configuration definition input 62 to generate a specific configuration object 63.

For example, at the conclusion of a design project, the design enterprise network 10 generates, or defines, standard installation software of a software instance to be installed at the laboratory enterprise network. The standard installation software is be handed to a user of the laboratory enterprise network 140. In another example, the standard installation software may be designed by and/or handed (for example, transmitted) to the laboratory enterprise network from a different network/entity.

The design enterprise network 10 generates at least one configuration identifier 68 that may be used by a user of the laboratory enterprise network 140 to obtain a configuration object 63 from the host 30.

The system comprises a laboratory enterprise network 140 of a laboratory or service user. The laboratory enterprise network may be controlled by the entity running the laboratory, laboratory entity or a hospital entity, which is different from the above mentioned manufacturer that controls the design enterprise network 10. According to an example, the laboratory enterprise network 140 is communicably coupled to an IVD network 20 comprising one or more IVD instruments 20ana, 20post, 20pre, 20trans. The laboratory enterprise network 140 is communicably coupled to the IVD network 20 by a networking connection 89, for example. The networking connection 89 may, in examples, be a LAN connection, Health Level 7 connection, or another proprietary communications protocol.

The system 8 comprises a host 30 that is communicably coupled to at least the design enterprise network 10 of the manufacturer and the laboratory enterprise network 140 of the laboratory or service user. For example, the host 30 is communicably coupled to the design enterprise network 10 and laboratory enterprise network 140 via a wide area communication network 7 such as the Internet. According to some examples, the design enterprise network 10 comprises the host 30. The host 30 can, for example, be a cloud computing service. The host 30 receives, from generator computing instance 14, of the design enterprise network 10 a configuration object 63.

The system 8 comprises a remote access network 40 that is communicably coupled to at least the design enterprise network 10 of the manufacturer and the laboratory enterprise network 140 of the laboratory or service user via the communication network 7. A remote computer 44 comprised within the remote access network 40 is, for example, capable of remotely accessing a node of the laboratory enterprise network 140, such as a software instance 144, after the configuration of a remote access server on the software instance 144.

In some examples, the remote computer 44 can access components of the IVD network 20 (such as at least one IVD instrument 20ana, 20post, 20pre, 20trans of the IVD network 20) via the remote server of the software instance 144, once the remote access server has been configured on the software instance 144).

Therefore the remote access network 40 can be used by remote service engineers to remotely configure and/or troubleshoot the laboratory enterprise network 140. In some examples, the remote access network 40 is operated by the manufacturer or service provider in control of the design enterprise network 10. In some examples, remote access network 40 is operated by a third-party consultant or maintenance provider.

In some examples, the remote access network 40 further comprises an archive of installers 66 based on the standard modules in the design enterprise network 10. This enables the field service engineer 59 to understand and model a specific software configuration that has been distributed to a laboratory enterprise network 140.

The system 8 comprises a data storage network 160. The data storage network 160 is communicably coupled to the other system 8 nodes via the WAN or LAN 7. The data storage network 160 may, in an example, be a cloud storage instance. The data storage network 160 comprises a gateway 162, and host computer 164 for performing administrative functions within the data storage network 160, and a data store 166. The data store 166 may comprise a wide range of data, such as securely held patient data, clinical trials results, historical IVD laboratory results or log files, and the like. For example, the software instance 144 of the laboratory enterprise network 140 may be configured to access historical patient data of a specific patient in the data store 166. The historical patient data from a patient is transmitted to a software analyser 20sw within the IVD network and combined with analytical results from the same patient, for example.

The system 8 comprises an analysis algorithm host 150. The analysis algorithm host may be, in examples, a cloud instance or a server. The analysis algorithm host 150 is communicably coupled to the WAN/LAN 7 via a gateway 152. An internal network 153 couples an analysis computing instance 154 to a data store 156. In an example, the data store 156 comprises one, or more, software algorithms which uses the results from an IVD instrument 20ana of an IVD network as input, possibly together with other input, for example, data received from the laboratory enterprise network 140 (for example, from the software instance 144), and/or the data storage network 160.

Figure 3:
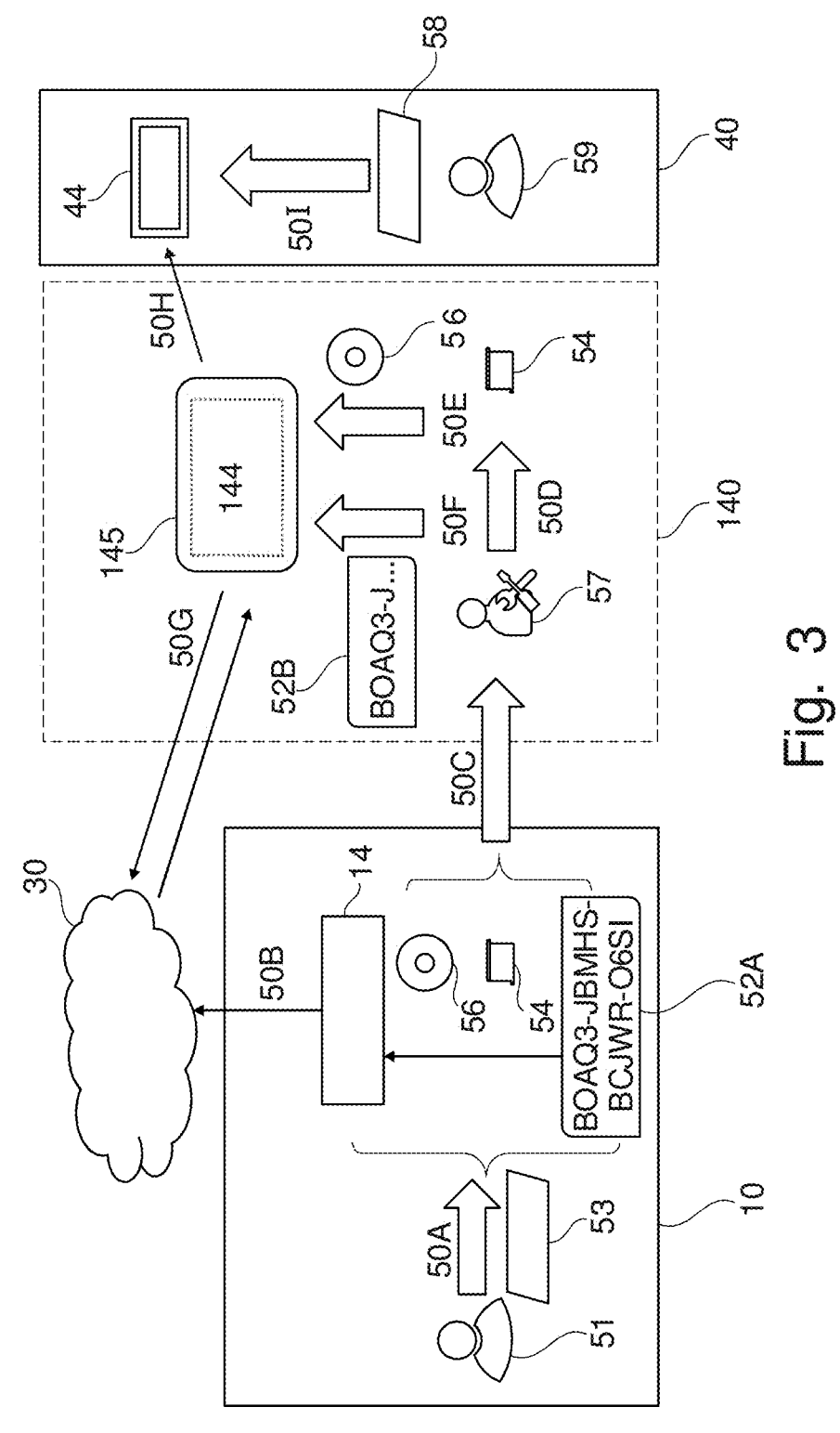
FIG. 3 schematically illustrates an example of remote software installation using the system according to the fifth aspect.

FIG. 3 schematically illustrates an example of remote software installation using the system according to the fifth aspect.

According to the workflow of FIG. 3, an engineer 51 authenticates themselves to a specific IVD laboratory design project. For example, the engineer 51 logs on to a generator computing instance 14 of a design enterprise network 10. Alternatively, the engineer 51 authenticates themselves to a specific IVD laboratory design project hosted by a cloud design service or a single design computer. In these case, the design enterprise network 10 can be considered to be the cloud design service or a single design computer. In an embodiment, the laboratory design project is accessible from within an authentication domain of an IVD laboratory manufacturer, or design consultancy.

The engineer 51 decides, based on the design of the at least a software instance 144 in a proposed, planned, or existing laboratory enterprise network, an appropriate standard software installation 56 for the software instance 144, and a subsequent specialized configuration definition input 62 of the standard software installation for the software instance 144, where the specialized configuration is typically applied following the standard installation. The engineer 51 captures the specialized configuration of the standard software installation in a configuration definition input 62.

As an example, the standard installation on the software instance 144 comprises a blank version of a remote networking server without remote access attributes necessary for a remote access computer 44 to access the software instance 144. In this case, the specialized configuration is, for example, remote access attributes such as login and networking details that the software instance 144 needs to be provisioned in order to communicate with a remote access computer 44, for example, for requesting and/or receiving IVD results from within the IVD network. However, the login and networking details are blank in the standard installation.

Upon provisioning, an operator of a computer in the remote network 40 is able to access the software instance 144.

According to another example, the standard installation on the software instance 144 comprises a healthcare specific software instance, for example, an edge component of a system for running medical algorithms using results from an IVD instrument 20*ana* of the IVD network.

The engineer 51 creates 50A, using the generator computing instance 14 of the design enterprise network 10, a configuration object 63 capable of modifying the standard software installation 56 to take into account specific requirements of the software instance 144 in the laboratory enterprise network 140.

The engineer 51 generates an identifier 52A that has a logical link to the configuration object 63 intended for deployment to the software instance 144 in the laboratory enterprise network 140. The engineer 51 typically generates the identifier 52A automatically, or with the partial assistance, of a web portal. According to an example, the identifier is an encrypted link to a specific location at the host 30 at which the configuration object 63 will be made available for download to the laboratory enterprise network 140.

The configuration object 63 contains configuration data specific to a laboratory site installation. The engineer 51 deploys the configuration object 63 to the host 30 or other persistent storage.

The engineer 51 can then organise the transfer 50C of the standard software installation to the site hosting the laboratory enterprise network 140 and the IVD network 20. The transfer may be performed using, for example, installation media 56 such as a CD-ROM, DVD, USB key, tape drive, or the like. Furthermore, standard product documentation, and or an installation guide 54A can be transferred with the installation media 56 comprising the standard software installation. Of course, in other cases the standard software installation can also be made available as a download from the host 30.

The engineer 51 also organises the transfer of the identifier 52A to the site hosting the laboratory enterprise network 140 and the IVD network 20. For example, the identifier 52A can be made available in a web portal, or can be transferred in plain text or encrypted print with the installation media 56.

At the site hosting the laboratory enterprise network 140 and the IVD network 20, the laboratory IT engineer 57 receives the installation media 56 and the identifier 52A. The laboratory IT engineer 57 follows 50D the installation guide 54B and installs 50E the standard version of the installation software 57B on a computing device 145 hosting the software instance 144 according to the installation guide 57A. The software instance may be, for example, an operating system or a virtualized computing instance, for example, to be used for a specific healthcare related purpose. The laboratory IT engineer 57 then enters 50F the configuration identifier 52B into a user interface of the computing device 145 or the software instance 144. In an example, the laboratory IT engineer 57 navigates to a webpage hosted by the host 30, and enters the configuration identifier 52B into a prompt on a webpage linked to the host 30. Alternatively, a software environment of the computing device 145 can request the configuration identifier 52B and communicate the configuration identifier 52B to the host 30.

Accordingly, the host 30 receives the identifier 52B. The host 30 checks the identifier 52B. If the identifier 52B corresponds to a configuration object 63 comprised in the host 30, and the configuration object 63 has been logically linked with the identifier 52B, the host communicates 50G the content of that configuration object 63 to the laboratory enterprise network 140, and specifically to the software instance 144. According to an example, the software instance 144 downloads the configuration object 63 from the host.

The standard software installation performed by the laboratory IT engineer 57 of the software instance 144 is configured according to the configuration object 63 downloaded from the host 30.

In a further example, following specific configuration of a remote networking server comprised in the software instance 144 according to the configuration object 63, the software instance 144 establishes a persistent communication link 50H with a remote network 40, for example, by using configurations according to the configuration object 63 (for example, specific remote access attributes enabling the establishment of the communication link). A field service engineer 59 authenticates 58 themselves on a remote computing device 44 of the remote network 40. The field service engineer 59 can access the configuration settings, or the operational environment, of the software instance 144, to make additional changes to the configuration in order to address a reported error, or in order to install new functionality, for example. In an example, the software instance 144 is a remote access server allowing the field service engineer 59 to remotely access an IVD network 20 (or its components) that is communicably coupled to the software instance 144. This enables the field service engineer 59 to perform diagnostic or configuration actions in the IVD network from a remote site. In an example, the configuration identifier 68 is only usable once.

In an example, the configuration identifier 68 is implemented as a one-time password. In an example, the identifier 68 is implemented as a time limited password.

Thus, an example of the functionality and purpose of the configuration identifier 68 is to enable remote access to at least one software instance 144 comprised in the laboratory enterprise network 140, and/or access to the IVD network 20. According to embodiments, remote access to an IVD instrument comprised in the IVD network 20 is possible. This enables, for example, data exchange with the IVD instrument, product maintenance, and/or automation.

In an example, when the laboratory IT engineer 57 enters the configuration identifier 68 into a user interface of the laboratory enterprise network 140, a field service engineer 59 is able to access the software instance 144 and/or other components the laboratory enterprise network 140 via a remote service platform. Of course, this is one example, and other product or operating system configuration values can be provided by the configuration identifier 68 as will be discussed subsequently. Beneficially, this allows remote access to be established for remote configuration and monitoring of IVD laboratory equipment. Furthermore, cloud-based systems or internal data sources of the IVD laboratory equipment can be accessed with minimal configuration burden placed on the laboratory IT engineer 57. The entry of the configuration identifier 68 also enables the transfer of security keys and certificates so that trusted communications can be established.

The software instance illustrated in FIG. 3 can perform many functions. In an embodiment, the software instance is a healthcare specific software product. The software instance 144 comprises one, or any combination, of (a) software or middleware for managing one or more IVD laboratory instruments 20_pre_, 20_ana_, 20_post_, 20_trans_, (b) software or middleware for managing (IVD) POC networks, (c) predictive maintenance software for IVD laboratory instruments and/or (IVD) POC instruments, (d) software for monitoring samples prior to a pre-analysis stage and/or pre-laboratory stage, (e) software for monitoring sample processing within an IVD laboratory, (f) software for managing a digital infrastructure of an IVD laboratory, (g) a (IVD) POC network; and/or a hospital, (h) an IVD databank, (i) a medical data datastore, (j) an EMR or EHR system, (k) software for IVD data transfer, (l) quality control software for IVD laboratory instruments or (IVD) POC instruments, (m) IVD laboratory instrument training software, (n) (IVD) POC instrument training software, (o) IVD instrument monitoring software, (p) IVD sample processing monitoring software, (q) IVD instrument management software, (r) IVD sample processing analysis software, (s) IVD instrument analysis software, (t) medical image processing software, (u) cyber security software for IVD laboratories and/or v) POC networks, (w) an operating system comprising medical algorithms, algorithms for analysing IVD laboratory and/or (v) POC network operations, (w) a healthcare information system, for example, a laboratory information system LIS or a hospital information system HIS. The software instance 144 may be and/or comprise an operating system or a hypervisor comprising at least one virtual machine, wherein the operating system resp. the virtual machine is used, for example, for a healthcare specific purpose (for example, running/hosting/supporting one of the examples given above).

Generating Identifier and Configuration Information

Figures 4A, 4B:
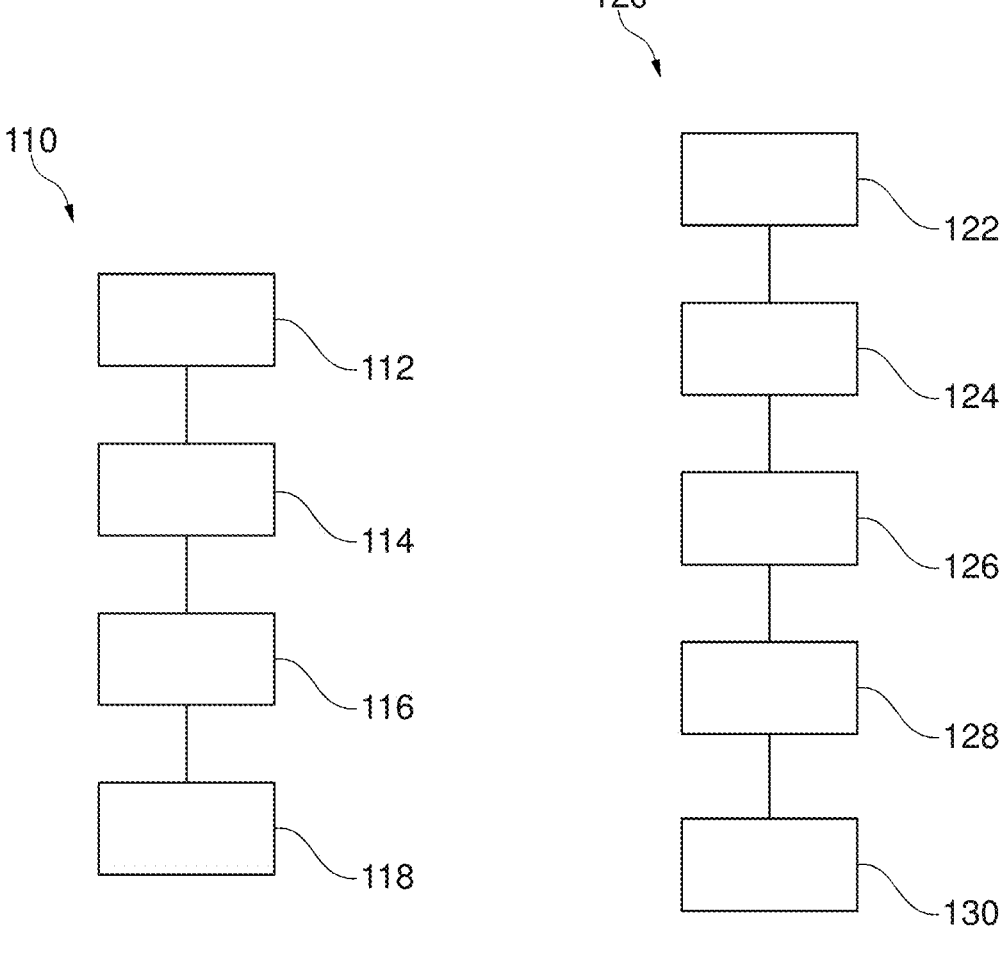
FIG. 4A schematically illustrates a computer implemented method according to the first aspect.
FIG. 4B schematically illustrates a computer implemented method according to the second aspect.

FIG. 4A schematically illustrates a computer implemented method according to the first aspect.

For example, the computer implemented method of the first aspect and its related embodiments is suitable for operating within a first network. The first network is a design enterprise network 10 comprising a generator computing instance 14 (design computer). In brief, the generator computing instance 14 receives a technical specification of at least the software instance 144 installed in, or intended to be installed in, the laboratory enterprise network 140. In an example where the software instance 144 is, or comprises, a remote access server, the technical specification comprises at least login and network address attributes that the remote access server hosted by the software instance 144 should be programmed with to enable remote access. The configuration definition input 62 is a means for transferring the technical specification into the generator computing instance 14 via a user interface. In the case of login and network address attributes, the configuration definition input 62 comprises, for example, alphanumeric login details and a network address.

The generator computing instance 14 generates a configuration object 63 capable of, for example, customising a standard installation for the software instance 144 in the laboratory enterprise network 140. The computer implemented method according to the first aspect also generates a configuration identifier 68 enabling a laboratory IT engineer responsible for the laboratory enterprise network 140 to trigger the execution of the configuration object 63 on the standard install software provided at the software instance 144. For example, the configuration object 63 can be provided by compressing, encoding, or parsing the configuration definition input 62 into a machine readable or interpretable format. According to an example, the configuration object 63 is in JSON format.

According to the first aspect, there is provided a computer implemented method 110 of a design enterprise network 10 for facilitating remote configuration of a software instance 144 comprised in a laboratory enterprise network 140, wherein the laboratory enterprise network 140 is communicably coupled to an in vitro diagnostics, IVD, network 20, wherein the IVD network 20 comprises at least one IVD instrument 20_pre_, 20_ana_, 20_post_, 20_trans_, and wherein the computer implemented method comprises:

obtaining 112, by a generator computing instance 14 comprised in a design enterprise network 10, a configuration definition input 62 for configuring the software instance 144;

generating 114, by the generator computing instance 14 comprised in the design enterprise network 10, a configuration object 63 based on the configuration definition input 62, wherein the configuration object 63 comprises computer readable data which is interpretable by the software instance 144 of the laboratory enterprise network 140 to define a configuration of the software instance 144;

generating 116, by the generator computing instance 14 comprised in the design enterprise network 10, a configuration identifier 68, wherein the configuration identifier 68 is logically linked 67 to the configuration object 63; and storing 118 the configuration object 63 in a host 30, wherein the host 30 is communicably coupled to the design enterprise network 10 and the laboratory enterprise network 140.

In an embodiment, the computing device of the design enterprise network 10 is configured to output the configuration identifier 68 to a user of at least one computing device 145 of the laboratory enterprise design network 140.

In embodiment, the computing device of the design enterprise network 10 is configured to output the configuration identifier 68 to a user of at least one computing device 145 of the laboratory enterprise design network 140. For example, the configuration identifier 68 is stored on a CD-ROM, DVD, USB drive, and the like.

Automated Configuration Using Identifier

FIG. 4B schematically illustrates a computer implemented method according to the second aspect.

The computer implemented method according to the second aspect, and its related embodiments, is suitable for operating within at least the laboratory enterprise network 140. Specifically, the method of the second aspect may be performed by a software instance 144 hosted by a computing device 145 of a laboratory enterprise network 140. The computer implemented method according to the second aspect enables the automated configuration of the software instance 144 by receiving a configuration identifier 68 from a user of a computing device in the laboratory enterprise network 140, and using the configuration identifier 68 to download and execute the configuration object generated according to the first aspect.

According to an embodiment, the computer implemented method 120 is a method of configuring a laboratory enterprise network 140.

According to the second aspect, there is provided a computer implemented method 120 for facilitating remote configuration of a software instance 144 in a laboratory enterprise network 140, wherein the laboratory enterprise network 140 is communicably coupled to an in vitro diagnostics, IVD, network 20, wherein the IVD network 20 comprises at least one in vitro diagnostic, IVD, instrument 20*pre*, 20*ana*, 20*post*, 20*trans*, wherein the method comprises:

obtaining 122, by the software instance 144 comprised in the laboratory enterprise network 140, a configuration identifier 68 generated by a generator computing instance 14 of a design enterprise network 10;

transmitting 124 the configuration identifier 68, by the software instance 144 of the laboratory enterprise network 140, to a host 30 that is communicably coupled to the design enterprise network 10 and the laboratory enterprise network 140;

receiving 126, from the host 30, a configuration object 63 that is logically linked to the configuration identifier 68, wherein the configuration object 63 comprises computer readable data which is interpretable by the software instance 144 of the laboratory enterprise network 140 that defines a configuration of the software instance 144 of the laboratory enterprise network 140, and wherein the configuration object 63 has been generated by the generator computing instance 14 of the design enterprise network 10 according to a configuration definition input 62 defining configuration data for facilitating the configuration of the software instance 144 of the laboratory enterprise network 140;

configuring 128 the software instance 144 of the laboratory enterprise network 140 according to the computer readable data of the configuration object 63; and operating 130 the software instance 144.

For example, the software instance is operated using the configuration according to the computer readable data of the configuration object 63. In an example, the software instance 144 is operated using remote access attributes such as login data and network address attributes according to the configuration definition input and/or comprised in the computer readable data.

Operating the software instance 144 includes messaging, requesting data, or downloading data, from an IVD instrument 20*ana* comprised in the IVD network 20. Operating the software instance 144 includes initiating, continuing with, or concluding an application installation on the software instance 144. Operating the software instance 144 includes launching, ending, or modifying a workflow in the IVD network 20. Operating the software instance 144 includes enabling at least one remote access computer 40 to access the software instance 144. Operating the software instance 144 includes causing the software instance 144 to access, and establish, a connection to one or more of a analysis algorithm host 150, a data storage network 160, or another instance accessible via a LAN or WAN connection.

According to an embodiment, the computer implemented method of second aspect 120 is a method of configuring a laboratory enterprise network 140 and/or a software instance 144.

Figure 5:
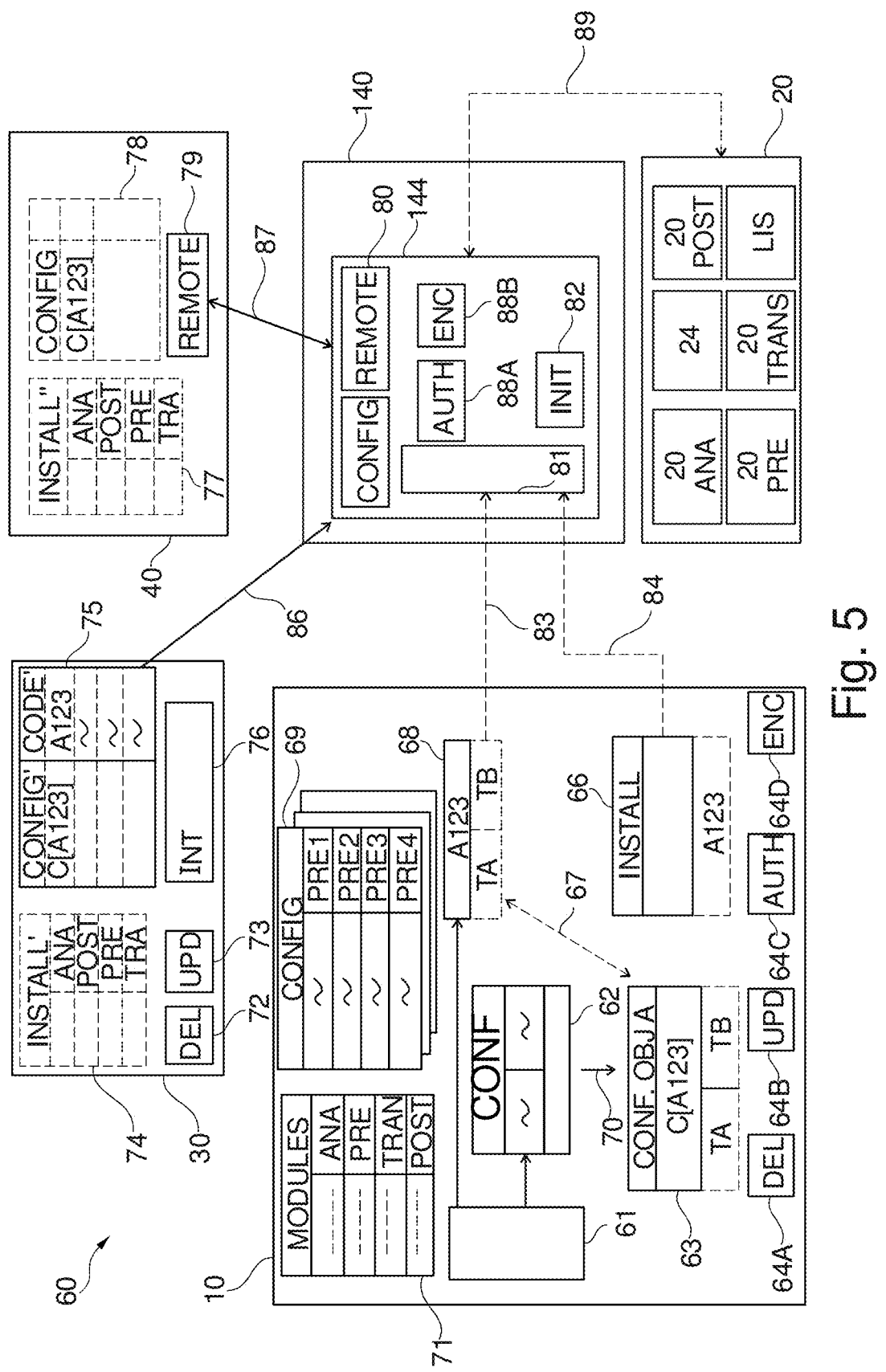
FIG. 5 schematically illustrates an example of a system model of the system according to the fifth aspect.

FIG. 5 schematically illustrates an example of a system model of the system.

The system model 60 of FIG. 5 illustrates the interactions of several different modules and data stores, not all of which are essential for certain embodiments described below. Accordingly, it is not essential that every element illustrated in FIG. 5 is present.

The generator computing instance 14 of the design enterprise network 10 is configured to coordinate the generation of the configuration object 63 that is logically linked to the configuration identifier 68 from the laboratory specific configuration provided as a configuration definition input 62 by a design engineer 51 (such as a software architect). One or more data stores 16 are communicably coupled with the generator computing instance 14 in order to provide information templates when generating a laboratory specific configuration definition input 62.

The system model 60 illustrated in FIG. 5 is one example of a system model that can be used to implement the techniques of the present specification, although a skilled person will appreciate that there are many variants to that presented.

In an example, the design enterprise network 10 comprises a configuration interface 61. For example, the configuration interface 61 is a web portal or a software application hosted natively by a configuration computer. A configuration engineer 51 uses the configuration interface 61 to generate an configuration definition input 62 of, for example, all or part of an IVD system or a point-of-care system that is being designed or reconfigured. The size and complexity of the configuration definition input 62 depends on the detail of the design that the configuration engineer 51 interacts with. The configuration definition input 62 defines how the standard installation software 56 should be configured, immediately after the standard installation software 56 has been installed on a software environment 144 of a computing device 145 of a laboratory enterprise network 140. Alternatively, the configuration definition input 62 can define a partial change to a previously executed installation of the software environment 144 based on standard installation software 56.

As will subsequently be explained, one use case is the installation of a remote access client on a software environment 144 of the laboratory enterprise network 140 so that a field service engineer 59 with access to a remote access computer 44 can remotely access the software instance 144 of the laboratory enterprise network 140 to perform further remote configuration.

Figure 9A:
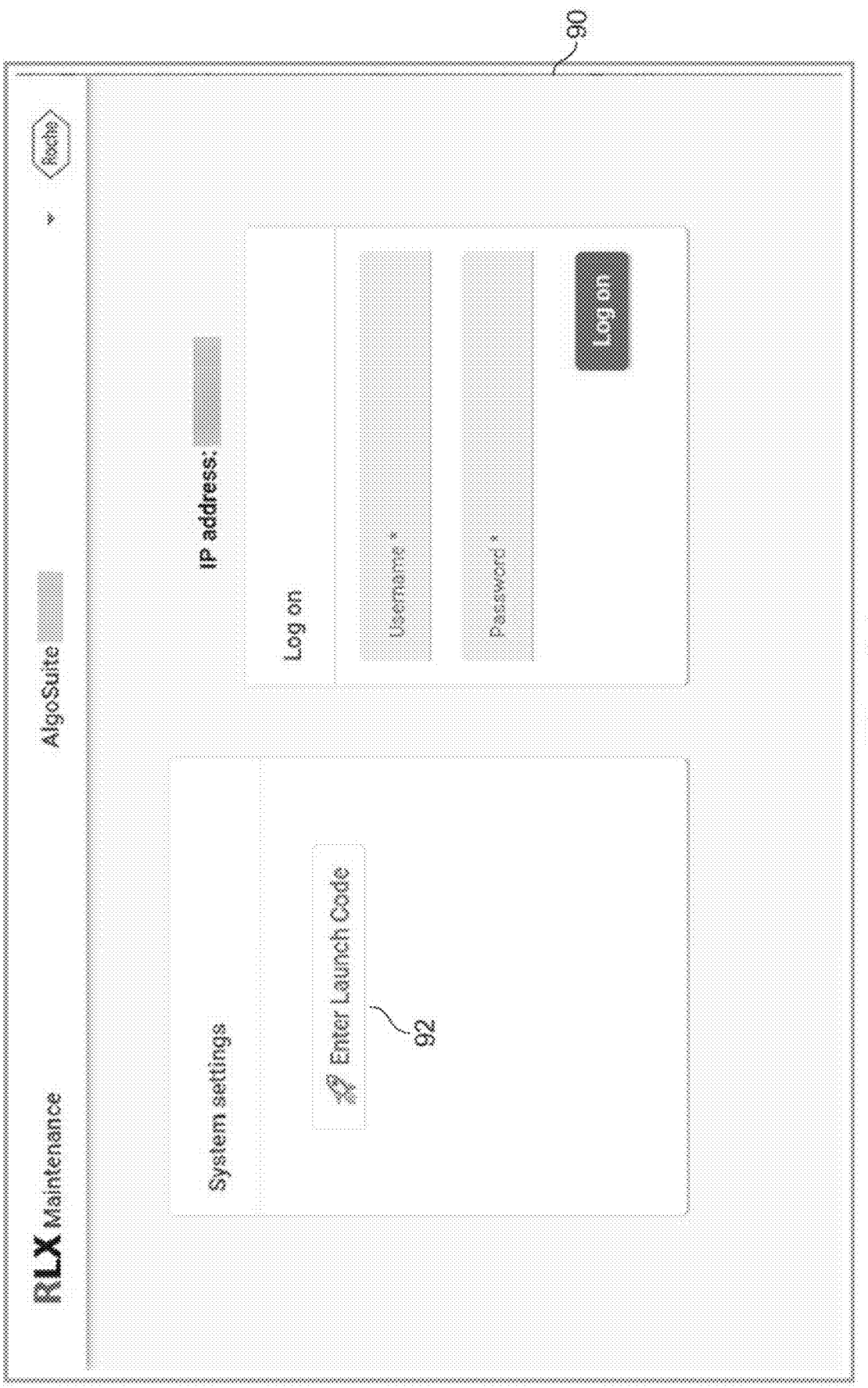
FIGS. 9A and 9B schematically illustrate a graphical user interface for remote software installation using the system according to the fifth aspect.

In an example, the installation media 56 comprises standard installation files of a remote access server. In this example, the configuration definition input 62 contains the login and network address attributes necessary to enable a remote networking connection 87 to be instantiated between the laboratory enterprise network 140 and the remote network 40. In this case, the configuration definition input 62 can be generated by the provision of the login and network address attributes through a web interface as shown in FIG. 9A, for example.

Returning to the system model 60 of FIG. 5, design enterprise network 10 is configured to generate 70 a configuration object 63 based on the configuration definition input 62. In an example, the configuration definition input 62 provided by the engineer 51 is automatically converted, as part of the generation process 70, into a JSON, XML, or YAML data object. The configuration object 63 is compiled so that it is readable by a configuration manager 81 comprised in the software instance 144 of the laboratory enterprise network 140. For example, if the software instance is an operating system, configuration manager 81 may be a package manager capable of interpreting the configuration object 63, and writing the content of the configuration object 63 to an addressed standard installation program of the software instance 44. As will be explained subsequently, the configuration manager 81 in laboratory enterprise network 140 directs the modification of standard software installations in the laboratory enterprise network 140.

Before, during, or after completing the configuration definition input 62, the engineer 51 is prompted, by the configuration interface 61, to provide a configuration identifier 68. The configuration identifier 68 is intended to be a simple and memorable code that a laboratory IT engineer 57 can use to initiate the automatic configuration of elements of the laboratory enterprise network 140 after the standard installation has been performed. The configuration interface 61 establishes a logical link 67 connecting the configuration identifier 68 and the configuration object 63. For example, the logical link 67 may be implemented by use of a database key.

The configuration object 63, once completed, is uploaded to the host 30 and stored in a set of configuration objects 75. The configuration identifier 68 is also transferred to the host 30 and is stored in a logically linked field of the set of configuration objects 75.

Other example use cases relate to the installation of standard firmware on the laboratory information system 5, and the configuration of laboratory instruments 20ana, 20pre, 20post and transport mechanisms 20trans. In this case, the configuration object 63 is substantially more complicated. In this embodiment, the order in which individual sub-entities of the configuration object 63 are applied in the laboratory enterprise network 140 can be specified in the configuration object 63, to prevent installation conflicts when the standardised software is configured in an incorrect order of priority.

The design enterprise network 10 comprises a register of standard modules 71. For each product that could be installed in an IVD network 20, the standard installation software is either stored in the register of standard modules 71, or a reference to the existence of the standard installation software is stored in the register of standard modules 71. Dependent on the configuration of the laboratory enterprise network 140 defined by an engineer 51 using the configuration interface 61, a software bill of materials (software BOM) is automatically designed. The software BOM may comprise standard installations of software (or firmware)

intended for use or installation in the laboratory enterprise network 140. The software BOM is optionally customizable after automatic generation.

In an embodiment, an installer 66 is provisioned based on a software configuration provided by an engineer 51 via the configuration interface 61. The installer 66 can comprise one or more software modules from the register of standard modules 71. For example, a plurality of standard modules may be loaded from the register of standard modules 71 and written onto a DVD disk 56. Alternatively, the plurality of standard modules may be loaded from the register of standard modules 71 onto a USB key. In another variant, the plurality of standard modules 71 may be uploaded from the register of standard module 71 to the host 30. The host 30 can comprise an installation mirror file 74, so that standard installation files can be downloaded from the host 34 installation on the second subsystem 20. Accordingly, the register of standard modules 71 enables an installer 66 of standard software modules to be assembled for distribution to, and/or installation on to a software instance 144 of a laboratory enterprise network 140.

In some embodiments, the configuration identifier 68 is incorporated into the installer 66. For example, once the laboratory IT engineer 57 completes the installation of standard software modules, the configuration manager 81 of the second subsystem 20 may automatically connect to the host 30 and request a download of the configuration object 63 from the host.

The provisioning of the installer 66 and its communication to the laboratory enterprise network 140 is optional, because a configuration object 63 that is logically linked to a configuration identifier 68 can be generated in the design enterprise network 10 in respect of a prospective partial or full configuration of a pre-existing set of software, firmware, and/or middleware in the laboratory enterprise network 140 and/or IVD network 20.

According to an embodiment, the design enterprise network 10 comprises a datastore containing a set of configuration templates 69. For a given element of the design of the laboratory enterprise network 140, the engineer 51 can obtain one or more configuration templates 69 via the configuration interface 61 to ensure that some aspects of the configuration definition input are appropriately standardised.

At least the configuration identifier 68 is provided 83 to the laboratory enterprise network 140. Typically, the configuration identifier 68 is provided 83 to the laboratory enterprise network 140 by a communication channel that at least partially avoids electronic communication networks. In an example, the communication identifier 68 can be entered into a user interface of the computing device 145 hosting the software instance 144 of the laboratory enterprise network 140 by a laboratory IT engineer 57.

The laboratory enterprise network 140 comprises a configuration manager 81. The configuration manager 81 can be provided as a software module in the computing device 145, or any other computing device that is a logical member of the laboratory enterprise network 140. The configuration manager 81 has a security privilege level enabling the configuration manager 81 to access at least the software instance 144 and to make configuration changes to it. For example, the configuration manager 81 is capable of writing to a registry file, an initialisation file (.ini) or other data storage structures containing configuration parameters of software or firmware capable of executing in an element of the laboratory enterprise network 140.

In an embodiment, the configuration manager 81 can direct the installation of the standard software components comprised in the installer 66. In an embodiment, the configuration manager 81 can check the installation of the standard software components comprised in the installer 66 by the laboratory IT engineer 57, and return an error message if an unexpected software configuration within the is detected in the laboratory enterprise network 140.

The software instance 144 of the laboratory enterprise network 140 may be required to execute an initialisation, or bootstrapping process. For example, after a standard installation of a remote access server onto the software instance 144, remote access to the remote access server is not be possible until a set of steps is completed within the laboratory enterprise network 140.

For example, an initialisation module 82 can prompt a user to complete configuration steps such as changing a keyboard layout option of a computing device, changing a time zone region or location in a software environment hosted by the computing device, changing a hostname of the computing device 145 hosting the remote access server, configuring DCHP or other networking settings (such as an IP address, a subnet mask, a gateway, or a DNS setting of a computing device in the second subsystem). As another example, an address of a NTP (Network Time Protocol) server is provided as an initialisation step.

As an example of initiating the customisation of the standard software installation, the configuration manager 81 prompts (for example, via a graphical user interface of the computing device 145 hosting the software instance 144) a laboratory IT engineer for the configuration identifier 68. The laboratory IT engineer enters the configuration identifier 68 into the prompt. In an alternative, the configuration identifier 68 is combined into the installer 66, such that the configuration manager 81 can obtain the identifier 68 when installing the standardised (uncustomised) software on one or more elements of the laboratory enterprise network 140.

The configuration manager 81 interrogates 85 the host 30 with the configuration identifier 68. The host 30 searches the set of configuration objects 75 for a configuration object 63 logically linked to the configuration identifier 68. If the host 30 finds a configuration object 63 that is logically linked to the configuration identifier 68, this configuration object 63 is downloaded 86 from the host 30 to a computing device 145 comprised within the laboratory enterprise network 140. For example, the configuration object 63 may be downloaded to a computing device 145 that is configured to host the software instance 144.

An example of a logical link between the configuration identifier 68 and the configuration object 63 is a database key, an index file, or a hash table.

The configuration manager 81 is configured to read the configuration object 63. Typically, reading the configuration object 63 comprises parsing a .JSON, .XML, or .YAML object.

In an example, the configuration manager 81 identifies which of a plurality of IVD instruments 20*ana* of the IVD network 20, that is communicably coupled to the laboratory enterprise network 140, require a configuration action to be performed based on the content of the configuration object 63.

In an embodiment, the configuration manager 81 is configured to communicate with each of the relevant IVD instruments 20*ana* to ensure that their file systems are capable of being written to. In an embodiment, the configuration manager 81 identifies a priority order in which the software instance 144, the IVD instruments 20*ana*, software modules, or firmware modules should be written to by the configuration manager 81.

The configuration manager 81 then performs a series of write actions to the software instance 144, the IVD instruments 20*ana*, software modules, or firmware modules, software modules, and/or firmware modules comprised in the laboratory enterprise network 140 and/or IVD network 20, as defined by the configuration object 63, so that by the end of the series of write actions, the apparatus, software modules, and/or firmware modules of the laboratory enterprise network 140 and/or IVD network 20 are provisioned with data as defined in the configuration definition input 62 provided by the engineer 51. In an embodiment, the configuration manager 81 reports, via a graphical user interface of a computing device 145 hosting the software instance 144 of the laboratory enterprise network 140, to a laboratory IT engineer 57 that the configuration process has concluded successfully or unsuccessfully.

In an embodiment, the configuration object 63 enables the customisation of a remote access server 80 in, or operable by, the software instance 144 of the laboratory enterprise network 140, so that the remote access server 80 is capable of establishing a remote networking connection 87 with a remote access client 79 of a remote access network 40. More specifically, the remote access network 40 is an IT network of a laboratory support system. For example, the remote access application 80 is the "Axeda" server application, or an XRDP server application. In another example, the remote access application 80 is a Windows Remote Desktop™ server.

Configuration Definition Input

Figure 6A:
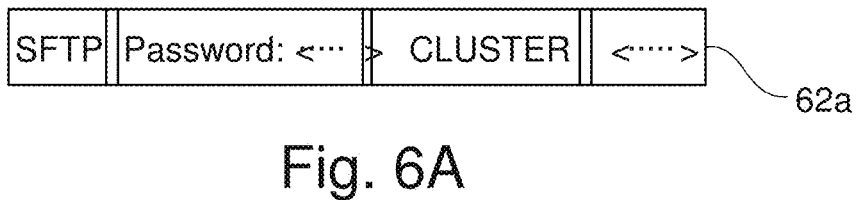
FIG. 6A schematically illustrates a first variant of a configuration definition input.
Figure 6B:
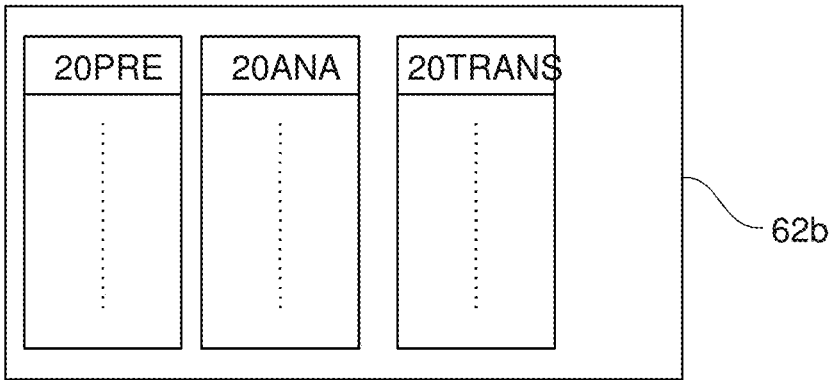
FIG. 6B schematically illustrates a first variant of a configuration definition input.

FIGS. 6A and 6B schematically illustrate two variants of a configuration definition input 62.

The scope of the configuration changes to the software instance 144 in the laboratory enterprise network 140 defined by the configuration object 63 is set by the structure of the configuration definition input 62 provided by the IT engineer using the design enterprise network 10.

FIG. 6A schematically illustrates an example of a limited configuration definition input 62 comprising changing one field in a configuration file of one software module, for example changing a port setting of an SSH communication client.

FIG. 6B schematically illustrates an example of a more complicated configuration definition input 62 comprising the files needed for automatic installation of a new analysis workflow across an entire network of analysis machines in an IVD network 20 that is communicably coupled to a laboratory enterprise network 140. Such a change in configuration would require the alteration of a plurality of fields of a plurality of configuration files associated with all apparatuses (20*pre*, 20*post*, 20*ana*, 20*trans*) in the second subsystem, managed using the software instance 144 of the laboratory enterprise network 140.

The configuration definition input 62 is generated, for example, using the configuration interface 61 of the design enterprise network 10. In an example, generating the configuration definition input 62 is an interactive process between the configuration interface 61 and the design engineer 51.

Referring briefly to FIGS. 11A-11C, this illustrates, for example, a graphical user interface for generating part of a configuration definition input 62 relevant to the Axeda™ remote access software. However, such an interface may enable the generation of a configuration definition input 62 for a wide range of software, hardware, and firmware arrangements, with examples discussed elsewhere in this specification.

In an example, the configuration changes enable remote access of a field service engineer 59 operable on a remote access network 40, to the software instance 144 comprised in the laboratory enterprise network 140. In this case, relatively limited alterations to the firewall settings (for example, changing allowed port numbers) of a gateway 142 of the laboratory enterprise network 140 and to networking settings of the computing device 145 and/or software instance 144 need to be performed.

In another example, to enable a field service engineer 59 to upload and download files from the software instance 144 of the laboratory enterprise network 140, a portion of the communication stack of the at software instance 144 may use STFP (Secure File Transfer Protocol). Therefore, the software instance 144, in embodiments, comprises an STFP client or server and the designation of an STFP password as the configuration definition input. In this example, the corresponding standard installation media for the laboratory enterprise network 140 can comprise the STFP client or server software, and the configuration definition input 62 includes networking addresses, login details, and passwords.

Furthermore, the configuration definition input 62 can comprise remote access attributes, such as login details and/or networking details for accessing a data storage network 160 that is communicably linked to software instance 144.

In an embodiment, the configuration object 63 is generated from the configuration definition input (62) and is formatted as a JSON object. A JSON string is more compact than other formats such as XML, for example, and can be read by a wide range of types of software. An example of a JSON formatted configuration object (63) is given below:

```
{
    "data": {
        "axeda": {
            "serial": "GW123456",
            "model": "axedaGW",
            "environment": "Production2"
        },
        "stp": {
            "password": "qwertz12345"
        },
        "cluster": { },
        "encryptedStorage": {
            "masterPassphrase": "qwertz12345",
            "keep": false
        }
    }
}
```

The foregoing JSON object is an example of a JSON object capable of configuring three software modules in a software instance 144 of the laboratory enterprise network 140. For example, the first software module of the software instance 144 to be configured from its standard installed state is the "Axeda" remote access module for which the software serial number, software model type, and environment name need to be provided as arguments during operation in order for the "Axeda" remote access applications to be initialised correctly.

The second originally installed software module of the software instance 144 is an "SFTP" application that must be provisioned with an appropriate password to enable the transfer of files to and from the software instance 144 of the laboratory enterprise network 140 using the SSH protocol.

The third originally installed module is a "cluster" access module for accessing a remote data storage network 160. The JSON configuration object 63 comprises a password to enable access of the software instance 144 to a storage cluster, for example.

In an embodiment, the configuration object 63 is formatted as an XML object. In an embodiment, the configuration object 63 is formatted as a YAML object. In an embodiment, the configuration object 63 is formatted as a .ini file.

In an embodiment, the configuration object 63 comprises computer executable instructions which, when executed or interpreted by the software instance 144, direct the installation of an operating system and/or application software on the software instance 144 of the laboratory enterprise network 140.

In this embodiment, the configuration object 63 comprises primitives giving folder locations and filenames to be used during an installation of standard software 56 on the software instance 144. A manufacturer may have specific conventions for the naming of folders and file name targets during installation of standard software 56 on software instance 144. Allowing the laboratory IT engineers to determine such folder and file name targets may subsequently lead to difficulties identifying expected folder and file name targets when remote service engineers attempt to perform remote maintenance. Therefore, standardising the install location folder and file name using the configuration object 63 in a way that is easily referenceable using a configuration identifier 68 can facilitate remote maintenance.

In an embodiment, the configuration object 63 comprises computer executable or interpretable instructions which, when executed, direct the reconfiguration of an operating system, virtual machine, hypervisor, and/or application software on the software instance 144 of the laboratory enterprise network 140.

In an embodiment, the configuration object 63 comprises computer executable instructions which, when executed by a hypervisor hosted by the software instance 144 of the laboratory enterprise network 140, instantiate a virtual machine hosted by the hypervisor, wherein the virtual machine comprises an operating system and/or application software. For example, if the software instance 144 hosts a Debian™ Linux™ operating system, the configuration object 63 may comprise commands for initialising the KVM (Kernel Virtual Machine) hypervisor virtualisation server. In turn, the standard software 56 may comprise at least one virtual machine that can be mounted and configured using commands comprised in the configuration object 63.

In an embodiment, the configuration object 63 comprises configuration settings of an installer 66 for a remote access application 80 enabling a remote computing device 44 to access the software instance 144 of the laboratory enterprise network 140 on which the remote access application 80 is installed.

In particular, the configuration object 63 comprises remote access attributes of a remote access application 80 located in the software instance 144. The remote access attributes are, for example, login and/or network address attributes of the remote access application 80. The remote access attributes enable, for example, a user of a remote computing device 44 comprised in a remote access network 40 to control a software instance 144 of the laboratory enterprise network 40. In an example, the remote access attributes further comprise IVD network access attributes (such as IVD network login and/or network address attributes, or proprietary IVD network protocol login information), enabling a user of a remote computing device 44 to configure elements within an IVD network 20 from the remote computing device 44 comprised in the remote access network 40.

For example, the installer 66 for a remote access application 80 may be configured to install Axeda™, or an XRDP server, or Microsoft™ RDP server, allowing a remote engineer to graphically log into, and operate, the software instance 144 from a remote network.

In an embodiment, the configuration object 63 contains settings enabling the software instance 144 to connect to at least one IVD network 20 comprising at least one IVD instrument 20pre, 20ana, 20post, 20trans. Therefore, a field service engineer 59 can access hardware, software, or firmware instances comprised in the one IVD network 20 from the remote computing device 44 one IVD network 20

In an embodiment, the configuration object 63 comprises at least one encryption key and/or at least one security certificate. According to this embodiment, using only the provided configuration identifier 68, the software instance 144 can be automatically provisioned with data elements for improving the standard of security. For example, at least one manufacturer specific encryption key and/or security certificate can be automatically provisioned on the software instance 144 without the active involvement of the laboratory IT engineer, and without needing to transfer the manufacturer specific encryption keys and/or security certificates on the medium carrying the standard software 56.

According to embodiments, the configuration definition input 62 and/or the computer readable data comprises remote access attributes of one, or more, or any combination of the following items: (i) a remote computing device 44 comprised in a remote access network 40, (ii) a further software instance 146 comprised in the laboratory enterprise network 140, (iii) an analysis algorithm host 150, (iv) a remote data storage network 160, (v) an IVD laboratory software instance 24 hosted by an IVD network 20, (vi) the IVD laboratory analytic instrument 20ana, (vii) an IVD laboratory pre-analytic instrument 20pre, (viii) an IVD transport instrument 20trans, (ix) an IVD laboratory post-analysis instrument 20post, (x) a middleware instance for managing an IVD network, (xi) a middleware instance for managing a (IVD) POC network, (xii) a (IVD) POC analyser, (xiii) a digital analytic software instance hosted by the IVD analytic network and configured to obtain data from at least one IVD analytic instrument, wherein the digital analytic software instance is configured to output an IVD analysis result, (xiv) an IVD inventory management solution, (xv) an IVD quality control instance, and (xvi) an IVD result validation instance.

According to embodiments, the configuration definition input 62 and/or the computer readable data comprises, in relation to the software instance 144, one, or any combination, of the items in the following list: a master password, an administrative user account identifier, an administrative account password, an organization name, a site name, a site description, a locale code, a country code, a locale date/time format, a locale time format.

According to embodiment, the configuration definition input 62 and/or the computer readable data comprises, in relation to the software instance 144, a default administrator email address, an administrator domain name, or a license server address.

According to an embodiment, the IVD network 20 comprises one, or any combination, of the listed items (i) to (xvi).

A skilled person will appreciate that although the configuration input definition 62 and the generation of the configuration object 63 have been discussed in relation to a limited set of software or middleware programs (for example, remote access programs), substantially any configurable aspect of software, middleware, or firmware present in a laboratory or point-of-care network can be automatically configuring according to the use of a configuration identifier 68 to download a configuration object 63 from a host 30.

Figure 7:
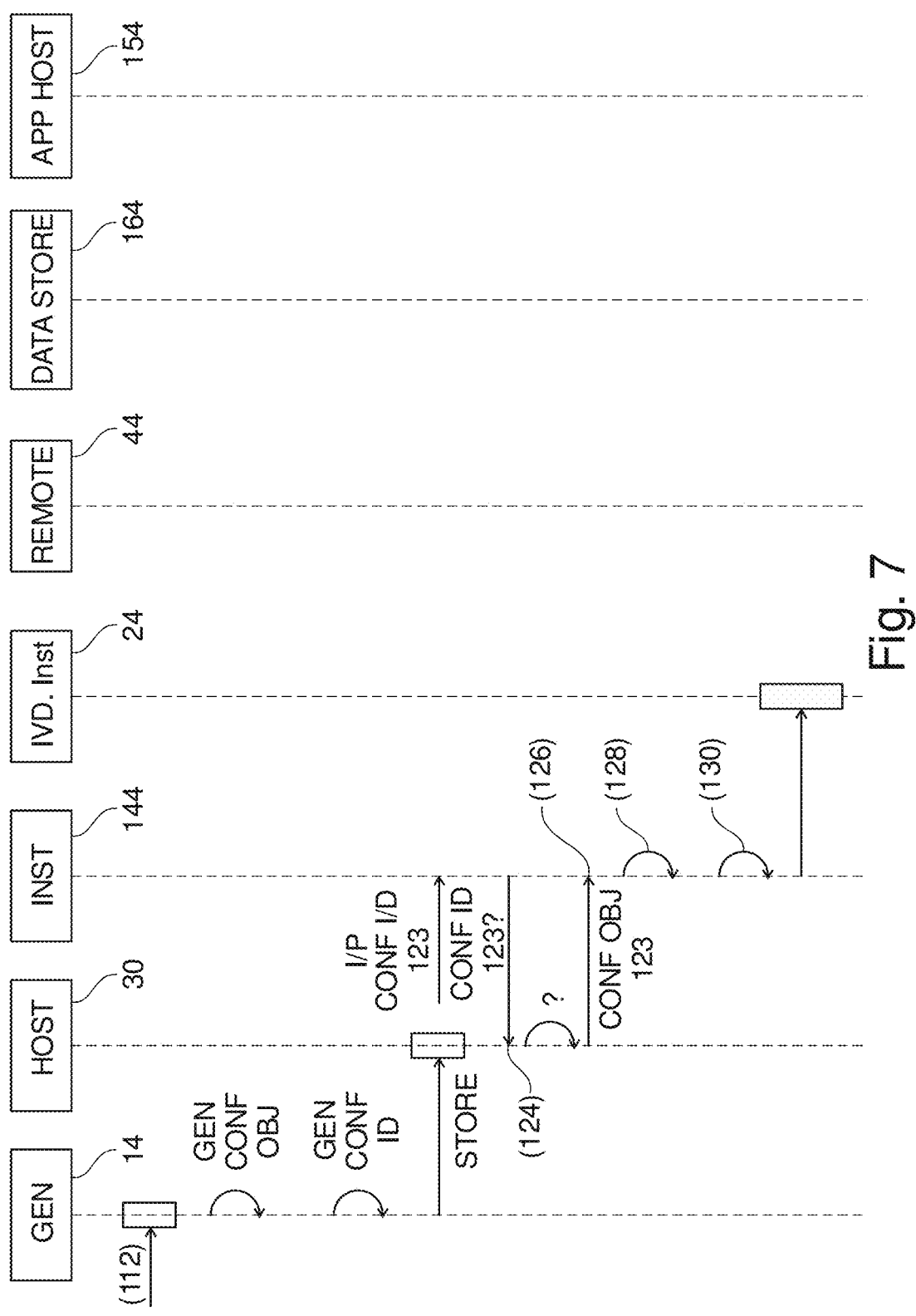
FIG. 7 schematically illustrates generating and distributing a configuration object.

FIG. 7 schematically illustrates an example of signalling in the system when generating and distributing a configuration object. In FIG. 7, like elements of FIG. 5 are illustrated with like reference numerals.

Installer

According to an embodiment, software instance 144 of the laboratory enterprise network 144 is configured to obtain computer executable instructions configured to execute an installer 66. The installer 66 is configured to partially configure a software environment of the software instance 144 of the laboratory enterprise network 144. After installation, the software environment 144 of the laboratory enterprise network 144 is configured according to the configuration object 63.

In an example, the installer 66 is a Debian package (or archive file) comprising libraries, documentation, and executable files associated with a program, or suite of programs, that are intended to be installed, or updated, on the software instance 144. An example, the configuration manager 81 of the software instance 144 can execute a package manager capable of unpacking the files comprised within installer 66 into binaries in a target directory of, for example, a Debian operating system. In an example, the installer 66 is composed from one or more standard modules 71 definable using the configuration interface 61 in the design enterprise network 10.

In an embodiment, when the configuration manager 81 of the software instance 144 receives the configuration identifier 68, the configuration manager 81 can begin installing the one or more packages comprised in the installer 66, and configuring them according to the machine readable instructions of the configuration object 63.

In another example, the installer 66 does not comprise libraries, documentation, and executable files. Instead, the installer 66 may comprise references to FTP locations (for example), where relevant software can be downloaded by the configuration manager 81 in the laboratory enterprise network 144. This enables the installation of the software instance 144 to be fully defined and configured at the design enterprise network 10, without needing to transfer large amount of data (such as the comprise libraries, documentation, and executable files). In an embodiment, when the configuration manager 81 of the laboratory enterprise network 144 receives the configuration identifier 68, the configuration manager 81 can begin downloading one or more packages referenced by the installer 66, and configuring them according to the machine readable instructions of the configuration object 63.

According to an embodiment, the installer 66 is configured to install a remote access application 80 enabling a remote computing device 44 external to the laboratory enterprise network 144 to perform a remote access session on the software instance 144 of the laboratory enterprise network 144.

For example, the remote access application 80 is the "Axeda" server application, or an XRDP server application. In another example, the remote access application 80 is a Windows Remote Desktop™ server. In this embodiment, the identifier 68 enables a laboratory IT engineer 57 to automatically configure a remote access application 80 on one or more software instances 144 of laboratory enterprise network 144 according to the configuration object 63. In embodiments, the remote access network 40 also comprises a mirror of the configuration object 63. Accordingly, when the remote access application 80 has been configured according to the configuration object 63, a field service engineer 59 can use a remote access client 79 based in the remote access network 40 to perform further remote configuration operations on the laboratory enterprise network 144 and/or IVD network 20.

According to an embodiment, the software instance 144 of the laboratory enterprise network 144 is configured to obtain initialization information of the software environment 144. The initialisation information comprises, for example, one, or any combination of, a time zone, a network setting, user credential, or an encryption configuration of the software instance 144 of the laboratory enterprise network 144.

In some examples, the configuration of software according to the definition of the configuration object 63 is not possible from an initial use of the software instance 144. For example, new IT equipment may be lacking a definition of such basic parameters as keyboard type and system time. In this case, a laboratory IT engineer 57 provides basic initialisation information via an initialisation module 82. The initialisation module 82 may, for example, be a wizard or in an initialisation file executed by IVD laboratory software instance 24, for example. The initialisation information provided by the laboratory IT engineer 57 enables a software environment or operating system of the software instance 144 to be bootstrapped to a point at which the installer 66 can be executed, and/or the identifier 68 can be input into a user interface of the IVD laboratory software instance 24 by the laboratory IT engineer 57.

According to an embodiment, the software instance 144 of the laboratory enterprise network 144 comprises a hypervisor, and the configuration object 63 is configured to instantiate, or configure, a virtual machine hosted by the hypervisor, wherein the virtual machine comprises an operating system and/or application software.

In the example of a Debian software environment, KVM (Kernel Virtual Machine) is an example of a virtualisation module for the Linux kernel that operates as a hypervisor. In examples, the installer 66 can comprise .ISO images that, when mounted by a hypervisor on the software instance 144, perform a specific function. For example, a number of different numerical analysis modules can be contained within a corresponding set of virtual machines. As the workload of an IVD laboratory changes, a different number or type of numerical analysis modules can be mounted software instance 144. The specific sequence and number of virtual machines required for various stages of an IVD laboratory workflow may be partially defined by information in the configuration object 63, for example.

Therefore, if there is a need to retask an IVD laboratory to a different testing workflow, a design engineer in the first subsystem can specify, via an updated entity definition 62, a reconfiguration of virtual machines required to perform numerical analysis that will satisfy the requirements of the new tasking. An identifier 68 is provided to a laboratory IT engineer 57, whereupon an updated configuration object 63 is downloaded by the configuration manager 81 in the laboratory enterprise network 140 and used by the software instance 144 to update the suite of virtual machines mounted on the software instance 144, as one example.

According to an embodiment, upon receiving the installer 66 at the laboratory enterprise network 144, a laboratory IT engineer 57, or an automated process in the configuration manager 81 may perform a checksum on the installer 66 files to verify their integrity.

Figure 9B:
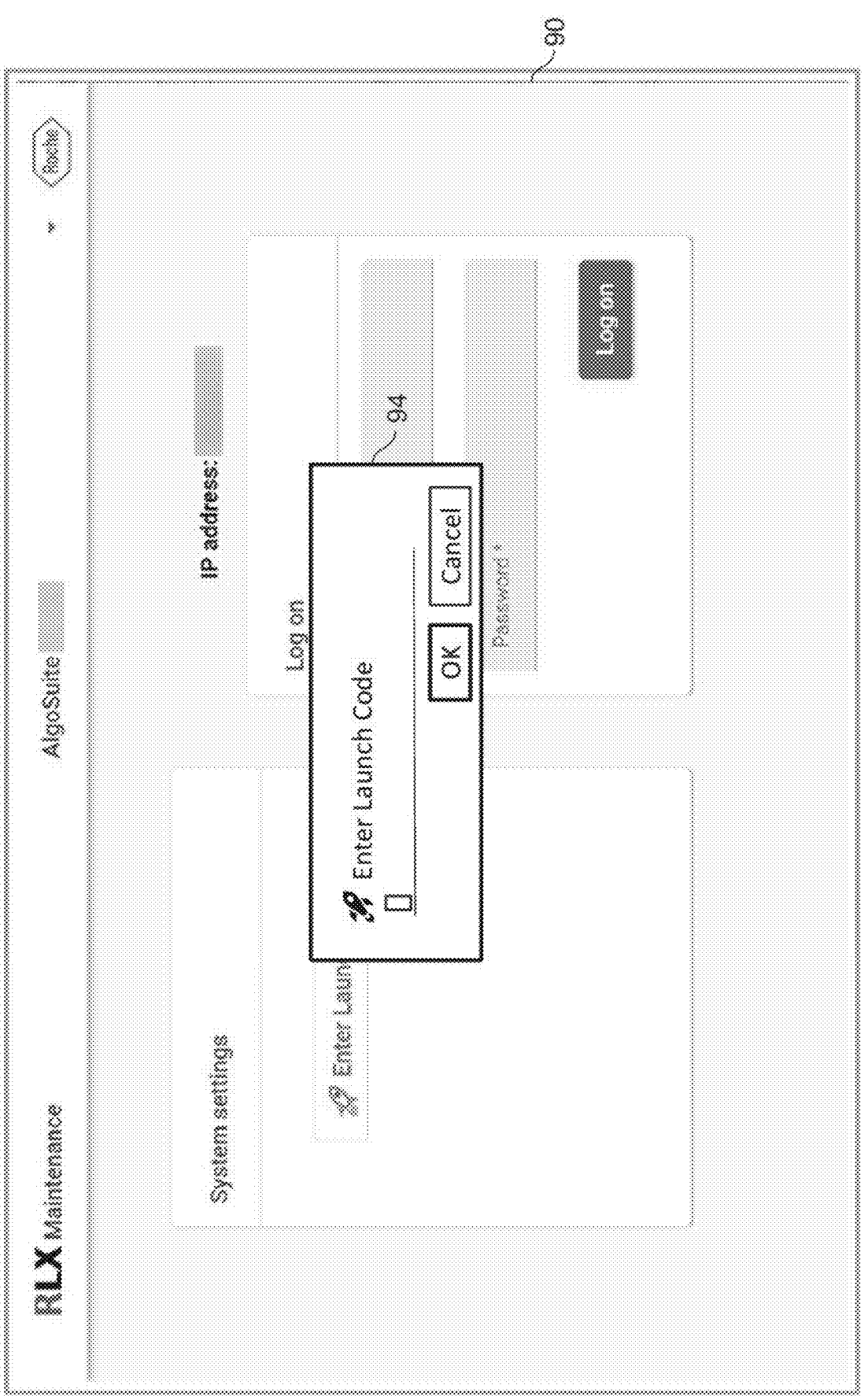

FIGS. 9A and 9B schematically illustrates a graphical user interface for remote software installation using the system according to the fifth aspect.

A landing page 90 that can be displayed by a user interface coupled to the software instance 144 in the laboratory enterprise network 144 comprises a button 92 enabling a user to select an option to enter a configuration identifier 68 (a "LaunchCode"). Upon actuation of the button 92, a dialog box 94 is presented prompting the user to enter the configuration identifier 68 (a "LaunchCode"). Following entry of the configuration identifier 68, the automated configuration is performed, for example, by the configuration manager 81.

Time Stamp

FIG. 11B illustrates an example of a graphical user interface that can be presented by a configuration interface of a design enterprise network 10 for setting, for example, an expiry date and time of a launch code and/or a configuration object 63.

According to an embodiment, the method comprises, when generating the configuration object 63, incorporating a first time reference TA into the configuration object 63 defining a time at which the configuration object 63, should be deleted from the host 30, and/or at least the software instance 144.

For example, the engineer 51 can define a time at which the customised installation defined by the configuration object 63 becomes obsolete, and should be deleted. Alternatively, the first time reference TA can be automatically included as part of a policy. The first time reference TA is included in the configuration object 63 at the time of generating the configuration object 63 from the configuration definition input 62.

The host 30 therefore comprises a persistent deletion process 72. The persistent deletion process 72 monitors each configuration object 63 stored in the set of configuration objects 75 of the host 30. If the persistent deletion process 72 detects a configuration object 63 with a first time reference TA but is older than reference time of the system (for example, a local time at the host 30), then the persistent deletion process 72 deletes the configuration object 63 and optionally sends a message to the configuration manager 81 in the laboratory enterprise network 140 and a message to the configuration interface 61 in the design enterprise network 10 announcing the deletion of the expired configuration object 63. In this case, the time at which the configuration object 63 is deleted is within the control of the engineer 50 one of the manufacturer. Potentially sensitive configuration settings are not, therefore, left on the host 30 permanently.

In an embodiment, the configuration identifier 68 comprises the first time reference.

In this example, a laboratory IT engineer 57 can clearly identify a time by which an installation process using the configuration object 63, and time limited by the first time reference TA, should be completed. For example, the first time reference TA comprises a date and a 24 hour time in DD-MM-YYYY-00:00 format. The first time reference TA is thus suffixed, prefixed, or otherwise included in the configuration identifier 68.

According to an embodiment, the method comprises, when generating the configuration object 63, incorporating a second time reference TB into the configuration object 63 defining a time at which the configuration object 63, was generated.

According to this variant, the laboratory IT engineer enters the identifier 68 and downloads 86 a configuration object 63 comprising the second time reference TB. For example, the second time reference TB comprises a date and a 24 hour time in DD-MM-YYYY-00:00 format stating the time that the configuration object 63 was generated. The configuration manager 81 reads the second time reference TB. In an embodiment, the configuration manager 81 can apply a policy that rejects configuration objects that have been generated too far into the past, and which allows configuration objects that have been generated more recently. A benefit is a reduced risk of installing an obsolete software configuration onto the laboratory enterprise network 140 or an IVD network 20, even though standard install media are already available.

In an embodiment, the configuration identifier 68 comprises the second time reference TA.

In this example, a laboratory IT engineer 57 can clearly identify, from the identifier 68, a time at which the configuration object 63 was generated. For example, the second time reference TB comprises a Gregorian date and a 24 hour time in DD-MM-YYYY-00:00 format. The second time reference TB is thus suffixed, prefixed, or otherwise included in the configuration identifier 68.

Embedding the Launch Code in the Installer

According to an embodiment, the identifier 68 is incorporated into the installer 66.

According to an embodiment, when installing the software environment on the software instance 144 of the laboratory enterprise network 140, the identifier 68 is detected within the installer 66.

According to an embodiment, after the identifier 68 has been detected within the installer 66, the software instance 144, or another computing device comprised within the laboratory enterprise network 140, communicates the identifier 68 to the host 30, to thus trigger a download of the configuration object 63.

According to this example, it may be beneficial to embed the identifier 68 in the plurality of modules 71 combined to form the installer 66. For example, an additional .ini file comprising the configuration identifier 68 is appended to the one or more set of packages comprising installer 66. This means that a separate step of communicating a configuration identifier 68 to a laboratory IT engineer 57 can be omitted, with the laboratory IT engineer 57 instead looking for the configuration identifier 68 in the list of packages forming the installer 66. In an embodiment, the configuration manager 81 in the network of the laboratory enterprise network 140, or another computing device in laboratory enterprise network 140, is configured to detect the configuration identifier 68 in the installer 66 and to communicate with the host 30 to obtain the configuration object 63 automatically.

Upon completion of a successful configuration, the configuration manager 81 or another element in the laboratory enterprise network 140 can message the host 30 to request the configuration object 63 used to configure the laboratory enterprise network 140 is deleted, or archived.

In another variant, the configuration identifier 68 is provided from the laboratory enterprise network 140 to the host 30. Provided the set of configuration objects 75 contains a configuration object 63 that is referenced by the configuration identifier 68, the chosen configuration object 63 is communicated to the laboratory enterprise network 140. According to this variant, the host 30 deletes the configuration object 63 that is referenced by the identifier 68 immediately after communicating the configuration object 63 to the second subsystem 20. In other words, the host 30 does not wait for positive confirmation from the second subsystem that the configuration according to the configuration object 63 has succeeded before deleting the configuration object 63. In the case of an error when configuring the laboratory enterprise network 140, the laboratory IT engineer 57 must request from the design enterprise network 10 a new identifier in respect of a duplicate set of configuration objects.

Authentication

In an embodiment, the configuration object 63 comprises secured data.

According to an embodiment, the generator computing instance 14 of the design enterprise network 10 is configured to generate, at the generator computing instance 14, challenge data that uniquely identifies the design enterprise network 10 as a trusted network, and to store the challenge data in the design enterprise network 10 and/or the host 30, and to incorporate the challenge data into the configuration object 63 to enable authentication of the configuration object 63 at the laboratory enterprise network 140. Therefore, the laboratory enterprise network 140 can verify that an item of configuration data 63 downloaded from host 30 was generated by the design enterprise network at the manufacturer, as opposed to an untrusted instance.

According to an embodiment, the software instance 144 of the laboratory enterprise network 140 further comprises:
   extracting, from the configuration object 63, challenge data;
   transmitting the extracted challenge data to the design enterprise network 10;
   comparing the extracted challenge data to original challenge data in the design enterprise network 10 used to generate the configuration object 63, wherein the original challenge data uniquely identifies the design enterprise network 10 as a trusted network; and
   based on the comparison between the extracted challenge data and the original challenge data, receiving, at the software instance 144 of the laboratory enterprise network 140 an authentication confirmation that the configuration object 63 received at the laboratory enterprise network 140 was generated by the design enterprise network 10.

Authentication instance 88A of the laboratory enterprise network 140 is configured to process challenge data received from to the design enterprise network 10.

For example, the authentication instance 64C of the design enterprise network 10 is configured to provide challenge data to the generator computing instance 14 on request. The challenge data is, for example, cryptographically based. In example, the challenge data is generated based on a SCRAM, OATH, or CHAP challenge response algorithm.

Figure 8:
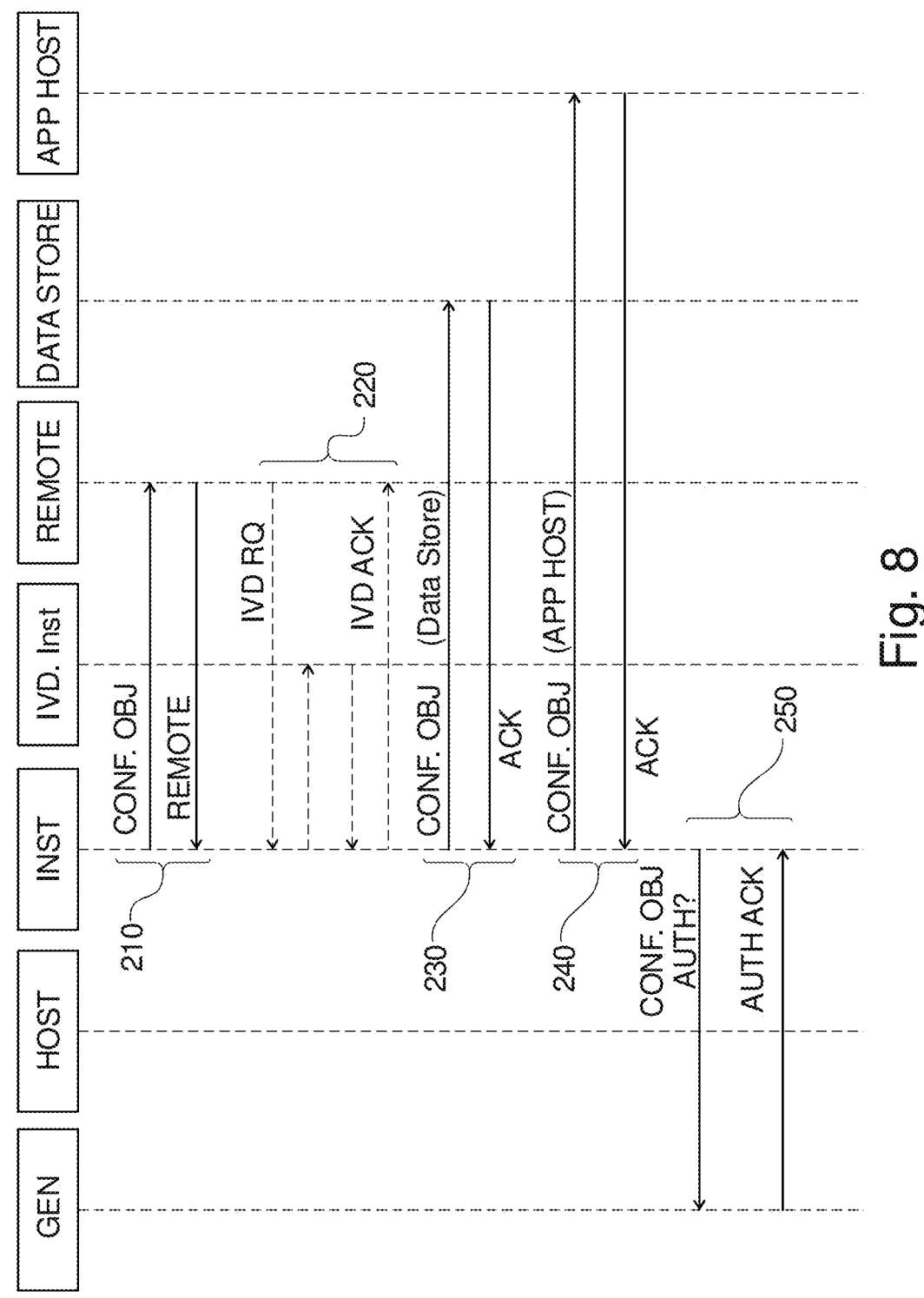
FIG. 8 schematically illustrates processes between a laboratory enterprise network and an IVD network.

FIG. 8 illustrates an example of authentication signalling at brace 250. In this example, the software instance 144 receives a configuration object 63 comprising challenge data. The software instance 144 transmits the challenge data to a generator computing instance 14 of a design enterprise network 10. The generator computing instance 14 of the design enterprise network 10 compares the challenge data with an original authentication challenge of the configuration object. The comparison succeeds, and the generator computing instance 14 signals an acknowledgement to the software instance 144. This enables the software instance

144 to continue applying the instructions of the configuration object 63. According to an example, the challenge data is a digital signature.

Encryption

According to an embodiment, there is provided a computer implemented method 110 of the generator computing instance 14 according to one of the preceding claims, further comprising:

encrypting the configuration object 63, wherein an encryption key used to encrypt the configuration object 63 is either the configuration identifier 68, or a user-specified key.

According to an embodiment, there is provided a computer implemented method 110 of the generator computing instance 14 comprising:

obtaining, at the software instance 144, a key for decrypting the configuration object 63 wherein the key is either the configuration identifier 68, or a user-specified key; and decrypting the configuration object 63 previously encrypted by the configuration identifier 68, or a user-specified key.

According to an embodiment of the software instance 144, there is provided a computer implemented method of:

obtaining, at the software instance 144, a key for decrypting the configuration object 63 wherein the key is either the configuration identifier 68 or a user-specified key; and decrypting the configuration object 63 previously encrypted by the configuration identifier 68, or a user-specified key.

The encryption and decryption may be based on symmetry or asymmetric encryption, for example. The key may have a length of 128 bits or fewer, 256 bits or fewer, 1024 bits or fewer, or 2048 bits or fewer.

The configuration object 63 could store security sensitive data, such as the login details and network addresses of the software instance 144 and/or a plurality of analyser in an IVD network 20. An encryption approach as detailed above allows the security sensitive data comprised in the configuration object 63 to be secured. This may relax the security requirements of the host 30, and the networks connecting the design enterprise network 10, the host 30, and the laboratory enterprise network 140 such that the configuration object 63 can be transmitted on public LAN or WAN networks.

Configuration Identifier

FIG. 11C illustrates an example of a configuration identifier 68, alternatively named as a "Launch Code". This is an example of a configuration identifier 68 that would be provided to an engineer 51 at the conclusion of the configuration process, for forwarding to a laboratory IT engineer 57.

In an embodiment, the configuration identifier 68 is one of a numeric, ASCII, or alphanumeric code, a visual code, a printed identifier, an email, an SMS message, or a voicemail message accessible at a predefined telephone number. Any format that is capable of uniquely identifying a configuration object 63 stored in a configuration object store 75 of the host 30 can be used as a configuration identifier 68. In some examples, the configuration identifier 68 may comprise at least 4, 8, 12, 16, 20, 24, 28, 32, 36, 40, 44, 48, or 52 alphanumeric or ASCII characters. A short code is easier for an individual to remember, although a longer code gives better security.

In an embodiment, the configuration identifier 68 enables the configuration object 63 to be communicated at a higher level of security compared to the installer 66.

In an embodiment, the configuration identifier 68 is sent from the design enterprise network 10 to the host 30 using the REST API.

In an embodiment, the configuration identifier 68 is a compound identifier comprising a plurality of unique codes. In a complicated installation process, it may be advantageous to allow the laboratory IT engineer some control over the staging of installation components. Accordingly, the installation can be defined by a plurality of configuration objects 63, with each configuration object 63 related to a corresponding unique configuration identifier 68.

The laboratory IT engineer may be provided with a list of a plurality of configuration identifiers 68 in priority order. The laboratory IT engineer, after having performed a standard installation on an software instance 144 using the installation media 56, may enter in the plurality of identifiers 68 in priority order. As the software instance 144 provides feedback that a successful configuration has resulted from the use of a first configuration identifier 68, the laboratory IT engineer may prompt a next configuration identifier 68 to move onto the next stage of system configuration. If the entry of a next configuration identifier 68 results in a failed configuration step, the laboratory IT engineer can contact a field service engineer 59 in order to address the failed configuration step remotely.

In an embodiment, a first configuration identifier 68 is logically linked to a first configuration object 63 defining the configuration of the software instance 144 in the laboratory enterprise network 140. The second configuration identifier 68 is logically linked to a second configuration object 68 defining the configuration of at least one at least one IVD instrument 20pre, 20ana, 20post, 20trans comprised in an in vitro diagnostics, IVD, network 20. Thus, a laboratory IT engineer has a degree of staging control over when software updates are applied to different networks, but the fine configuration may still be performed by a remote engineer.

Delete Configuration Object after Install

According to an embodiment, the design enterprise network 10 is configured to receive, from the software instance 144 of the laboratory enterprise network 140, a request that the configuration object 63 is deleted, and/or archived, from the host 30; and, upon receipt of the request, a message is sent from the design enterprise network 20 to the host 30, causing the host 30 to delete and/or archive the configuration object 63 from the set of configuration objects 75 in the host 30.

According to an embodiment, the software instance 144 of the laboratory enterprise network 140 is configured to check, that the configuration object 63 has deployed successfully. If the at least one configuration object 63 has deployed successfully, a message is sent from the software instance 144 to a generator computing instance 14 in the design enterprise network 10, and/or the host 30, to request that the configuration object 63 is deleted, and/or archived, from the host 30.

According to an embodiment, in the design enterprise network 10, upon detecting, via the host 30, that the configuration object 63 has been downloaded to the laboratory enterprise network 140, a message is sent from the design enterprise network 10 to the host 30, causing the host 30 to delete the configuration object 63 from the set of configuration objects 75 in the host.

According to an embodiment, the host 30 detects that the configuration object 63 has been downloaded to the laboratory enterprise network 140, and deletes the configuration object 63 from the host 30.

In some examples, it is beneficial to remove the configuration object 63 from the host 30, when the configuration object 63 is no longer needed. For example, the original configuration definition input 62 and/or the configuration object 63 may still be available in the design enterprise network 10. Exposing the configuration object 63 in the host 30 longer than is necessary could open up the possibility that an unintended download of the configuration object 63 is made by a party that obtained the launch code.

Therefore, the software instance 144 of the laboratory enterprise network 140 can detect that the configuration object 63 has deployed successfully by, for example, performing a hash over the memory locations of the software instance 144 relevant to applications (such s a remote networking tool) that have been configured by the configuration object 63. Alternatively, the configuration manager 81 may be configured to maintain a log file of configuration actions required by the configuration object 63, and the success or failure of each action required by the configuration object 63.

Remote Access

FIG. 9B schematically illustrates a graphical user interface for remote software installation using the system according to the fifth aspect. In particular, FIG. 9B a illustrates dialog box 94 is presented prompting the user to enter the configuration identifier 68 (a "LaunchCode").

According to an embodiment, the software instance 144 of the laboratory enterprise network 140 obtains computer readable instructions configured to execute an installer 66. The installer 66 is configured to install the software instance 144 on a computing device 145 of the laboratory enterprise network 140. After installation of the software instance 144, the user is prompted to provide the configuration identifier 68. For example, the configuration object 63 is downloaded from the host 30 based on the configuration identifier 68. The software instance 144 is then configured according to the configuration object 63.

According to an embodiment, the installer 66 is configured to install a remote access application 80 enabling a remote computing device 44 external to the laboratory enterprise network 140 to perform a remote access session on the software instance 144 of the laboratory enterprise network 140, and/or wherein the configuration object 63 comprises remote access attributes of the remote computing device 44.

According to an embodiment, the software instance 144 performs the steps of:

establishing a remote network connection between the software instance 144 of the laboratory enterprise network 140 and a remote computing device 44 comprised in a remote access network 40 based on remote access attributes of the remote computing device 44 comprised in the configuration object 63, receiving, at the software instance 144, at least one remote networking command from the remote computing device 44, and operating the software instance 144 based on commands issued by the remote computing device 44 of the remote access network 40.

For example, a remote networking server 80 may be installed on the software instance 144, or a computing device such as the IVD laboratory software instance 24 of the IVD network 20. For example, the remote access application 80 is the "Axeda" server application, or an XRDP server application. In another example, the remote access application 80 is a Windows Remote Desktop™ server.

A standard version of the remote networking server 80 is, firstly, automatically installed on the laboratory enterprise network 140. A remote field service engineer 59 can then access one or more software instances 144 of the laboratory enterprise network 144 from the remote computing device 44.

According to an embodiment, the remote computing device 44 can access at least one node of the IVD network, such as an IVD instrument 20*pre*, 20*ana*, 20*post*, 20*trans*, via the remote access application 80 comprised in the software instance 144 of the laboratory enterprise network 140.

This means that a field service engineer 59 does not need to travel to the site of the IVD laboratory in order to perform diagnostics, troubleshooting, or other software configuration.

According to an embodiment, the configuration object 63 comprises computer readable data comprising remote access attributes of one, or any combination of (a) to (p): (a) a remote computing device 44 comprised in a remote access network 40, (b) a further software instance 146 comprised in the laboratory enterprise network 140, (c) an analysis algorithm host 150, (d) a remote data storage network 160, (e) an IVD laboratory software instance 24 hosted by an IVD network 20, (f) the IVD laboratory analytic instrument 20*ana*, (g) an IVD laboratory pre-analytic instrument 20*pre*, (h) an IVD transport instrument 20*trans*, (i) an IVD laboratory post-analysis instrument 20*post*, (j) a middleware instance for managing an IVD laboratory network, (k) a middleware instance for managing a (IVD) POC network, (l) a (IVD) POC analyser, (m) a digital analytic software instance hosted by the IVD analytic network and configured to obtain data from at least one IVD analytic instrument, wherein the digital analytic software instance is configured to output an IVD analysis result, (n) an IVD inventory management solution, (o) an IVD quality control instance, (p) an IVD result validation instance. For example, the remote access attributes are login and/or network address attributes of any one of (a) to (p).

According to an embodiment, the computer implemented method further comprises:

establishing a network connection between the software instance 144 of the laboratory enterprise network 140 and one, or any combination, of the further instances (a) to (p) using corresponding the computer readable data, for example, remote access attributes, comprised in the configuration object 63; and exchanging data between one, or any combination, of the further instances (a) to (p) via the software instance 144 and/or the remote computing device 44 of the remote access network 40.

FIG. 8 illustrates signalling to establish a remote access session. In brace 210, the software instance 144 communicates a configuration object 63 to the remote access network 40. The configuration object 63 may comprise, for example, login and networking details of a remote access instance of the software instance 144. The remote access network 40 establishes a remote networking connection to the software instance 144.

Also illustrated in FIG. 8, brace 220, is an example of the remote access network 40 accessing an IVD instrument 20*ana* of an IVD network 20 subsequently to the establishment of a remote networking connection in 210. For example, an operator of a computing device comprised in the remote access network can utilize the remote connection to the software instance 144 established in 210 to access an IVD instrument 20*ana* that is comprised within an IVD network 20 that is communicably coupled to the laboratory enterprise network 140. In some examples, the operator of a computing device comprised in the remote access network is restricted to reading information from the IVD instrument 20ana, for example to diagnose a noncompliance with the IVD instrument 20ana. In other examples, the operator of a computing device comprised in the remote access network may configure the IVD instrument 20ana from the remote access network.

Brace 230 illustrates a software instance 144 requesting data from a data store.

Brace 240 illustrates a software instance 240 sensing configuration information to a cloud software analyser host.

Updating after Change of Configuration Input Definition

According to an embodiment, the method 110 further comprises altering, by the generator computing instance 14 of the design enterprise network 10, the configuration input definition 62, updating, by the generator computing instance 14, the configuration object 63 according to the altered configuration input definition 62, updating the configuration object 63 in the host 30; and messaging the software instance 144 of the laboratory enterprise network to report that the configuration object 63 has been altered by the generator computing instance 14.

According to an embodiment, the method 120 further comprises detecting that the configuration object 63 corresponding to the configuration identifier 68 in the host 30 that is communicably coupled to the design enterprise network 10 and laboratory enterprise network 140 has been altered by a computer of the design enterprise network 10, and reprovisioning the configuration object 63 comprised in the software instance of the laboratory enterprise network 140 with the altered configuration object.

In some embodiments, the configuration specified by the configuration object 63 is a one-time process, implying that a new configuration object 63 is required for each new configuration identifier 68 that is entered.

In other embodiments, entering the configuration identifier 68 into a computing device of the second subsystem and obtaining the configuration object 63 from the host 30 can be viewed as establishing a persistent relationship between the laboratory enterprise network 140 and the host 30 and/or the design functions of the design enterprise network 10. For example, as a design IT engineer 51 makes minor design changes to solve bugs or address "zero day" security matters, the design IT engineer 51 can modify the configuration input definition 62 relevant to a given software instance 144 of the laboratory enterprise network 140, or a connected IVD network 20, for example.

Referring briefly to FIG. 5, the design enterprise network 10 comprises an updater module 64B. The host 73 comprises an updater module 73.

Therefore the updater 65 in the design enterprise network 10 can detect that a configuration input definition 62 has been updated. Following regeneration of the configuration object 63 linked to the configuration input definition 62, the regenerated configuration object 63 is pushed to the set of configuration objects 75 in the host 30. The updater module 64B of the design enterprise network 10 may also message the configuration manager 81 of the software instance 144 comprised in the laboratory enterprise network 140 to announce that an updated configuration relevant to the second subsystem is available in the host.

The laboratory IT engineer 57 may, for example, choose when to apply the regenerated configuration object 63 in the laboratory enterprise network 140. Alternatively, automated logic in the configuration manager 81 can determine a time at which it is safe to apply the regenerated configuration object 63 in the laboratory enterprise network 140 automatically. For example, if the configuration manager 81 identifies that the configuration object 63 requires reconfiguring an operational IVD instrument of an IVD network 20 linked to the laboratory enterprise network 140, the configuration manager 81 does not automatically apply the regenerated configuration object 63 in the second subsystem 20 if analytical tests are in the process of being performed by the operational IVD instrument 20ana of the IVD network 20.

According to an embodiment, a change of the configuration input definition 62 causes a new configuration object 63 to be generated, that is logically linked with a new configuration identifier 68. The new configuration identifier 68 is communicated to the laboratory IT engineer 57 via an agreed communication channel, to enable a reconfiguration of, for example, at least one software instance 144 of the laboratory enterprise network 140.

FIG. 8 illustrates signalling between a software instance 144 and a plurality of instruments of an IVD network 20.

Figures 10A, 10B:
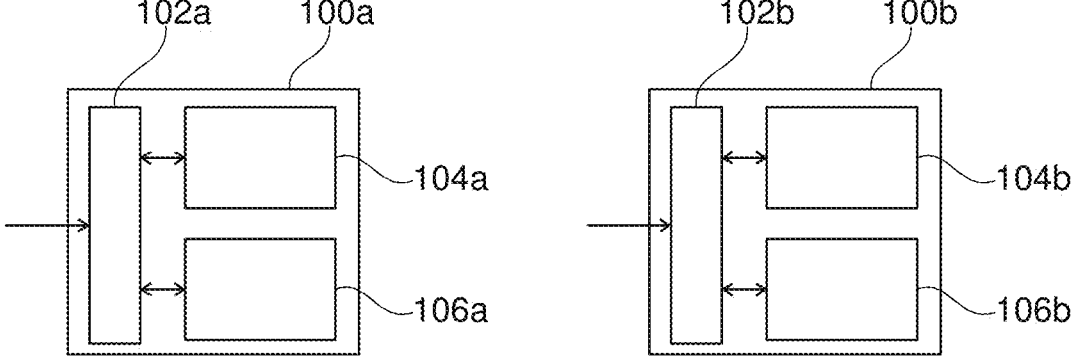
FIG. 10A schematically illustrates an apparatus according to the third aspect.
FIG. 10B schematically illustrates an apparatus according to the fourth aspect.

FIG. 10A illustrates generator computing device according to the third aspect.

According to the third aspect, there is provided a generator computing device 14, 100a comprising: a communications interface 102a, a memory 104a and a processor 106a, wherein the processor 106a is configured to perform the computer implemented method 110 according to first aspect, or its embodiments.

For example, the generator computing device according to the first aspect is a personal computer (PC), an enterprise computer comprised within a design enterprise network 10, or an enterprise computer providing access to a cloud design instance. The cloud design instance is configured to receive a configuration definition input 62 and to upload a corresponding configuration object into the host 30, for example.

The generator computing device 14, 100a further comprises a user interface, such as a monitor, computer mouse, and computer keyboard, to enable a user to define the configuration definition input 62.

FIG. 10B illustrates computing device according to the fourth aspect.

According to a fourth aspect, there is provided a computing device 145, 100b comprising a communications interface 102b, a memory 104b, and a processor 106b. The processor 106b is configured to perform the computer implemented method according to the second aspect, or its embodiments.

For example, the computing device 145, 100b according to the fourth aspect is a personal computer (PC), a bare metal server, an enterprise computer comprised within the laboratory enterprise network 140, or an enterprise computer providing access to a cloud instance. The cloud instance is configured to administrate the laboratory enterprise network 140, for example.

The communications interface may comprise one or more of a WAN or LAN adaptor.

Furthermore, the communications interface may comprise a unit configured to communicate with at least one IVD instrument of an IVD network 20. For example, the unit may comprise a communications adaptor capable of utilizing the health level 7 (HL7) protocol.

The computing device 145, 100b further comprises a user interface, such as a monitor, computer mouse, and computer keyboard, to enable a user to enter the configuration identifier 68. Furthermore, the user interface may comprise a camera, to enable the configuration identifier 68 to be scanned from a piece of paper, for example.

According to a fifth aspect, there is provided a system.

The system 8 comprises a design enterprise network 10, wherein the design enterprise network 10 comprises a gateway 12, a generator computing instance 14 communicably coupled to the gateway 12, wherein the generator computing instance 14 is configured to perform the computer-implemented method 110 according to the first aspect, or its embodiments.

The system 8 further comprises a laboratory enterprise network 140, wherein the laboratory enterprise network 140 comprises: a gateway 142, a computing device 145 communicably coupled to the gateway, wherein the computing device 145 is configured to host a software instance 144 communicably coupled to the gateway 142 of the laboratory enterprise network 140. The software instance 144 is configured to perform the computer-implemented method 120 according to the second aspect, or its embodiments. The laboratory enterprise network 140 is communicably coupled to an IVD network 20, wherein the IVD network 20 comprises an IVD instrument 20pre, 20ana, 20post, 20trans, for example, including at least IVD analyser (20ana) such as or a POC device; and an IVD network gateway 22 (which, for example, may be part of the IVD instrument).

The system 8 further comprises a host 30. The host 30 comprises a host gateway 32, and a data store 34 communicably coupled to the host gateway via a host network 31; and wherein the system further comprises: a communication network 7 configured to communicably couple the design enterprise network 10, the laboratory enterprise network 140, the host 30, the IVD network 20 comprising the IVD instrument 20pre, 20ana, 20post, 20trans, for example, an IVD analyser (20ana) such as an IVD laboratory analytic instrument or a POC device.

The communication network 7 may, for example, comprise one or more of a local area network LAN provided over, for example, an ethernet network, a Wi-Fi network, and/or a communication network 7 such as the Internet. The communications network may comprise a Mobile Telecommunications network such as a 3G, 4G, or 5G system, and/or a hospital PACS network.

Optionally, the communication network 7 interfaces with an internal communications system of a hospital or medical facility. The internal communications system may be considered to be an intranet, for example. A firewall and other security measures known to a person skilled in the art may be placed in between the internal communications system and the communications network 7 to ensure security and confidentiality.

In an embodiment, the computing device 145 of the laboratory enterprise network 140 configured to host software instance 145 is configured to remotely access and configure one, or more, of: a medical analyser, IVD laboratory software instance 24 of the IVD network 20 hosting middleware configured to operate a network of medical analysers, and/or a computer of the IVD network 20 configured to execute laboratory or medical analysis software, an IVD analyser, a laboratory information system, and/or a hospital information system.

According to an embodiment, the design enterprise network 10 is a computer network of a manufacturer system configuration facility.

According to an embodiment, the laboratory enterprise network 140 is a computer network of an analysis laboratory, a hospital, or a point of care device network.

According to an embodiment, the remote network 40 is a computer network of a remote engineering maintenance facility.

In an example, the communication network 7 is a WAN and/or a LAN. In an example, the an IVD network gateway 22 is configured to communicate with the IVD network 20 using a specialized format for communicating with analytical instruments, such as the "health level 7" (HL7) format.

According to an embodiment, the system 8 further comprises a remote access network 40, wherein the remote access network comprises a remote gateway 42 communicably coupled to the communication network 7. The system 8 further comprises a remote computing device 44 configured to communicate with the software instance 144 of the laboratory enterprise network 140. The remote computing device 44 of the remote access network 40 is configured to establish a remote network connection between the software instance 144 of the laboratory enterprise network 140 and a remote computing device 44 comprised in the remote access network 40 based on remote access attributes of the remote computing device 44 comprised in the configuration object 63, and operate the software instance 144 based on commands issued by the remote computing device 44 of the remote access network 40.

According to a seventh aspect, there is provided a computer program element comprising computer-readable instructions which, when being executed by a computer, performs the method of the fifth aspect, or its embodiments.

According to an eighth aspect, there is provided a computer readable medium comprising the computer program element according to the seventh aspect.

Further disclosed is a computer program including computer-executable instructions for performing the method according to the present disclosure in one or more of the embodiments enclosed herein when the program is executed on a computer or computer network. Specifically, the computer program may be stored on a computer-readable data carrier. In other examples, the computer program can be Cloud-based computer programs. Thus, specifically, one, more than one or even all of method steps as disclosed herein may be performed by using a computer or a computer network, preferably by using a computer program.

Further disclosed is a computer program product having program code, in order to perform the method according to the present disclosure in one or more of the embodiments enclosed herein when the program is executed on a computer or computer network. Specifically, the program code may be stored on a computer-readable data carrier.

Further disclosed is a data carrier having a data structure stored thereon, which, after loading into a computer or computer network, such as into a working memory or main memory of the computer or computer network, may execute the method according to one or more of the embodiments disclosed herein.

Further disclosed is a computer program product with program code stored on a machine-readable carrier, in order to perform the method according to one or more of the embodiments disclosed herein, when the program is executed on a computer or computer network. Specifically, the computer program product may be distributed over a data network.

Further disclosed is a modulated data signal which contains instructions readable by a computer system or computer network, for performing the method according to one or more of the embodiments disclosed herein.

Further disclosed is a computer loadable data structure that is adapted to perform the method according to one of the embodiments described in this description while the data structure is being executed on a computer.

The features disclosed in the foregoing description, or the claims to follow, or in the drawings, whether described as apparatus features or in terms of means for performing a disclosed function, or in terms of method or process steps, may separately, or in any combination, used for providing the invention. While the invention has been described in terms of the embodiments of this description, a skilled person will be able to provide many equivalent modifications and variations based on this disclosure. Exemplary embodiments disclosed above are therefore for the purposes of illustration, and are not limiting. Changes to the embodiments described in this description can be provided without changing the spirit and scope of the invention. Paragraph headings introduced herein are not intended to limit the subject matter described. In this specification and the appended claims, the words "comprise" and "include" and their variations should be understood to imply the inclusion of a stated feature, or step or group of features, but not the exclusion of any other features.

The invention claimed is:

1. A computer implemented method of a design enterprise network for facilitating remote configuration of a software instance comprised in a laboratory enterprise network, wherein the laboratory enterprise network is communicably coupled to an in vitro diagnostics (IVD) network, wherein the IVD network comprises at least one IVD instrument, and wherein the computer implemented method comprises:

obtaining, by a generator computing instance comprised in the design enterprise network, a configuration definition input for configuring the software instance;

generating, by the generator computing instance comprised in the design enterprise network, a configuration object based on the configuration definition input, wherein the configuration object comprises computer readable data which is interpretable by the software instance of the laboratory enterprise network to define a configuration of the software instance;

generating, by the generator computing instance comprised in the design enterprise network, a configuration identifier, wherein the configuration identifier is logically linked to the configuration object;

storing the configuration object in a host, wherein the host is communicably coupled to the design enterprise network and the laboratory enterprise network;

configuring the software instance according to the computer readable data of the configuration object; and operating the software instance.

2. The computer implemented method according to claim 1, further comprising:

detecting, via the host, that the configuration object has been downloaded to the laboratory enterprise network; and deleting the configuration object from the host.

3. The computer implemented method according to claim 1, wherein the configuration identifier is one of a numeric or alphanumeric code, a visual code, an image, an email, an SMS message, or a voicemail message accessible at a predefined telephone number.

4. The computer implemented method according to claim 1, wherein the configuration definition input comprises remote access attributes of one, or more, of (i) to (xvi) as follows:

(i) a remote computing device comprised in a remote access network;

(ii) a further software instance comprised in the laboratory enterprise network;

(iii) an analysis algorithm host-;

(iv) a remote data storage network;

(v) an IVD laboratory software instance hosted by the IVD network;

(vi) a further IVD laboratory analytic instrument comprised in the IVD network;

(vii) an IVD laboratory pre-analytic instrument comprised in the IVD network;

(viii) an IVD transport instrument comprised in the IVD network;

(ix) an IVD laboratory post-analysis instrument comprised in the IVD network;

(x) a middleware instance for managing an IVD laboratory network;

(xi) a middleware instance for managing a POC network;

(xii) a POC analyser;

(xiii) a digital analytic software instance hosted by the IVD analytic network that obtains data from at least one IVD analytic instrument, wherein the digital analytic software instance outputs an IVD analysis result;

(xiv) an IVD inventory management solution;

(xv) an IVD quality control instance; or (xvi) an IVD result validation instance.

5. A generator computing device comprising:

a communications interface;

a memory; and a processor, wherein the processor is configured to perform the computer implemented method according to claim 1.

6. A computer implemented method for facilitating remote configuration of a software instance in a laboratory enterprise network, wherein the laboratory enterprise network is communicably coupled to an in vitro diagnostics (IVD) network, wherein the IVD network comprises at least one in vitro diagnostic (IVD) instrument, wherein the method comprises:

obtaining, by the software instance comprised in the laboratory enterprise network, a configuration identifier generated by a generator computing instance of a design enterprise network;

transmitting the configuration identifier, by the software instance of the laboratory enterprise network, to a host that is communicably coupled to the design enterprise network and the laboratory enterprise network;

receiving, from the host, a configuration object that is logically linked to the configuration identifier, wherein the configuration object comprises computer readable data which is interpretable by the software instance of the laboratory enterprise network that defines a configuration of the software instance of the laboratory enterprise network, and wherein the configuration object has been generated by the generator computing instance of the design enterprise network according to a configuration definition input defining configuration data for facilitating the configuration of the software instance of the laboratory enterprise network;

configuring the software instance of the laboratory enterprise network according to the computer readable data of the configuration object; and operating the software instance.

7. The computer implemented method according to claim 6, further comprising:

establishing a remote network connection between the software instance of the laboratory enterprise network and a remote computing device comprised in the remote access network based on remote access attributes of the remote computing device comprised in the configuration object;

receiving, at the software instance, at least one remote networking command from the remote computing device; and operating the software instance based on commands issued by the remote computing device of the remote access network.

8. The computer implemented method according to claim 6, wherein the configuration object comprises computer readable data comprising remote access attributes of one, or any combination, of one, or more, of a) to p) as follows:

a) a remote computing device comprised in a remote access network;

b) a further software instance comprised in the laboratory enterprise network;

c) an analysis algorithm host;

d) a remote data storage network;

e) an IVD laboratory software instance hosted by the IVD network;

f) the IVD laboratory analytic instrument comprised in the IVD network;

g) an IVD laboratory pre-analytic instrument comprised in the IVD network;

h) an IVD transport instrument comprised in the IVD network;

i) an IVD laboratory post-analysis instrument comprised in the IVD network;

j) a middleware instance for managing an IVD laboratory network-;

k) a middleware instance for managing a (IVD) POC network;

l) a (IVD) POC analyser;

m) a digital analytic software instance hosted by the IVD analytic network that obtains data from at least one IVD analytic instrument, wherein the digital analytic software instance outputs an IVD analysis result;

n) an IVD inventory management solution;

o) an IVD quality control instance; and p) an IVD result validation instance;

and the computer implemented method further comprises:

establishing a network connection between the software instance of the laboratory enterprise network and one, or any combination, of the further instances a) to p) using the corresponding remote access attributes, comprised in the configuration object; and exchanging data between one, or any combination, of the further instances a) to p) via one or more of the software instance or the remote computing device of the remote access network.

9. The computer implemented method claim 6, wherein the software instance comprises one or more items selected from the following list:

a) software or middleware for managing one or more IVD laboratory instruments comprised in the IVD network;

b) software or middleware for managing POC networks;

c) predictive maintenance software for at least one of IVD laboratory instruments or POC instruments;

d) software for monitoring samples prior to at least one of a pre-analysis stage or pre-laboratory stage;

e) software for monitoring sample processing within an IVD laboratory;

f) software for managing a digital infrastructure of an IVD laboratory, g) a POC network;

h) an IVD databank;

i) a medical data datastore;

j) an EMR or EHR system;

k) software for IVD data transfer;

l) quality control software for IVD laboratory instruments or POC instruments;

m) IVD laboratory instrument training software;

n) POC instrument training software;

o) IVD instrument monitoring software;

p) IVD sample processing monitoring software;

q) IVD instrument management software;

r) IVD sample processing analysis software;

s) IVD instrument analysis software;

t) medical image processing software;

u) cyber security software for at least one of IVD laboratories or POC networks;

v) an operating system comprising at least one of medical algorithms or algorithms for analysing at least one of IVD laboratory or POC network operations;

w) a healthcare information system, x) a laboratory information system, or y) a hospital information system.

10. The computer implemented method of claim 6, further comprising:

obtaining, by the software instance of the laboratory enterprise network, computer readable instructions that execute an installer, wherein the installer installs the software instance on a computing device of the laboratory enterprise network; and after installation of the software instance, prompting a user to provide the configuration identifier.

11. The computer implemented method according to claim 10, wherein at least one of:

the installer installs a remote access application enabling a remote computing device external to the laboratory enterprise network to perform a remote access session on the software instance of the laboratory enterprise network, or the configuration object comprises remote access attributes of the remote computing device.

12. A computing device comprising:

a communications interface;

a memory; and a processor, wherein the processor is configured to perform the computer implemented method according to claim 6.

13. A system comprising:

a design enterprise network, wherein the design enterprise network comprises:

a gateway;

a generator computing instance communicably coupled to the gateway, wherein the generator computing instance performs the computer-implemented method of the generator computing instance according to claim 1; and wherein the system further comprises:

a laboratory enterprise network, wherein the laboratory enterprise network comprises:

a gateway;

a computing device communicably coupled to the gateway, wherein the computing device is configured to host a software instance communicably coupled to the gateway of the laboratory enterprise network, wherein the software instance is configured to perform the computer-implemented method of the software instance according to claim 1;

wherein the system further comprises:

an IVD network, wherein the IVD network comprises:
    an IVD instrument; and
    an IVD network gateway;
wherein the IVD network is communicably coupled to the
    laboratory enterprise network;
wherein the system further comprises:
    a host, wherein the host comprises:
        a host gateway; and
        a data store communicably coupled to the host
           gateway via a host network; and wherein the
           system further comprises:
           a communication network configured to commu-
               nicably couple the design enterprise network,
               the laboratory enterprise network, the host, and
               the IVD network comprising the IVD instru-
               ment.

14. A non-transitory computer readable medium compris-
ing instructions which, when being executed by a computer,
performs the computer implemented method according
claim 1.

\* \* \* \* \*